United States Patent
Fong et al.

(10) Patent No.: US 9,510,755 B2
(45) Date of Patent: Dec. 6, 2016

(54) ECG MONITORING SYTSTEM WITH DOCKING STATION

(75) Inventors: Shannon Fong, San Francisco, CA (US); Chuni Kao, Sammamish, WA (US); Earl Herleikson, Cinebar, WA (US); William McCoy, Spokane, WA (US); Victor Iseli, Edmonds, WA (US); Michael Crawford, Auburn, WA (US); Brett Cross, Redwood City, CA (US); Jacco Eerden, Kirkland, WA (US); Douglas Denney, Sammamish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1307 days.

(21) Appl. No.: 12/921,801

(22) PCT Filed: Mar. 4, 2009
(Under 37 CFR 1.47)

(86) PCT No.: PCT/IB2009/050880
§ 371 (c)(1),
(2), (4) Date: Dec. 3, 2010

(87) PCT Pub. No.: WO2009/112973
PCT Pub. Date: Sep. 17, 2009

(65) Prior Publication Data
US 2011/0208076 A1  Aug. 25, 2011

Related U.S. Application Data

(60) Provisional application No. 61/035,070, filed on Mar. 10, 2008.

(51) Int. Cl.
*A61B 5/04* (2006.01)
*A61B 5/00* (2006.01)
(Continued)

(52) U.S. Cl.
CPC ........... *A61B 5/0006* (2013.01); *A61B 5/0205* (2013.01); *A61B 5/0404* (2013.01); *A61B 5/0432* (2013.01); *A61B 2560/0456* (2013.01); *G06F 19/3418* (2013.01)

(58) Field of Classification Search
CPC  A61B 5/0006; A61B 5/0205; A61B 5/0432; A61B 5/0404; A61B 2560/0456
USPC ................................. 600/509; 128/903, 904
See application file for complete search history.

(56) References Cited

U.S. PATENT DOCUMENTS 5,558,638 A * 9/1996 Evers et al. .................... 604/66
6,819,013 B2 * 11/2004 Kelly et al. .................. 307/104
(Continued)

FOREIGN PATENT DOCUMENTS

| CN | 2169249 Y | 6/1994 |
|---|---|---|
| CN | 1692746 A | 11/2005 |

(Continued)

*Primary Examiner* — Mallika D Fairchild

(57) ABSTRACT

An ECG monitoring system for ambulatory patients includes a battery-powered ECG monitor which attaches to a patient to receive patient electrical signals. A processor continuously processes received ECG signals and stores the signals in memory in the monitor. A wireless transceiver in the ECG monitor transmits the processed ECG signals to a cellphone handset. The battery of the monitor is recharged when the monitor is properly positioned in a charging dock, during which time the ECG signals are sent to the cellphone handset. Preferably the cellphone handset is recharged by the charging dock at the same time. At the conclusion of recharging and data transfer the monitor performs a self-test. A light on the charging dock is illuminated if any of the operations performed while the monitor is docked is unsuccessful.

17 Claims, 35 Drawing Sheets

(51) Int. Cl.
*A61B 5/0205* (2006.01)
*A61B 5/0404* (2006.01)
*A61B 5/0432* (2006.01)
*G06F 19/00* (2011.01)

(56) References Cited

U.S. PATENT DOCUMENTS

| | | | |
|---|---|---|---|
| 2004/0127802 A1* | 7/2004 | Istvan et al. | 600/509 |
| 2004/0147818 A1 | 7/2004 | Levy et al. | |
| 2004/0215814 A1* | 10/2004 | Park | 709/236 |
| 2006/0084883 A1* | 4/2006 | Linker | 600/518 |

FOREIGN PATENT DOCUMENTS

| | | |
|---|---|---|
| CN | 1859868 A | 11/2006 |
| DE | 199117766 A | 2/2000 |
| DE | 19832361 A | 9/2000 |
| JP | 2005253609 | 9/2005 |
| WO | 9424929 A | 11/1994 |
| WO | 0047108 A | 8/2000 |
| WO | 0128495 A | 4/2001 |
| WO | 0241773 A | 5/2002 |
| WO | 03015005 A | 2/2003 |
| WO | 03061465 A | 7/2003 |
| WO | 2005055822 A1 | 6/2005 |
| WO | 2007063436 A2 | 6/2007 |
| WO | 2007066270 A2 | 6/2007 |
| WO | 2007104116 A2 | 9/2007 |
| WO | 2007140069 A1 | 12/2007 |
| WO | 2008056309 A2 | 5/2008 |
| WO | 2008068695 A1 | 6/2008 |
| WO | 2009019649 A1 | 2/2009 |

\* cited by examiner

Template Information:

Template description: Arrythmia patient

Configuration:

Ventricular fibrillation:
| | | | |
|---|---|---|---|
| Heart rate greater than or equal to | 110 | BPM for | 15 seconds. |
| Document event: | ☑ Every | | 30 minutes. |
| Priority: | Urgent | | |

High heart rate:
| | | | |
|---|---|---|---|
| Heart rate greater than or equal to | 160 | BPM for | 5 seconds. |
| Document event: | ☑ Every | | 30 minutes. |
| | ☐ When heart rate increases by | | 0 BPM. |
| Priority: | Medium | | |

Low heart rate:
| | | | |
|---|---|---|---|
| Heart rate less than or equal to | 35 | BPM for | 5 minutes. |
| Document event: | ☑ Every | | 30 minutes. |
| | ☐ When heart rate decreases by | | 0 BPM. |
| Priority: | None | | |

Very low heart rate:
| | | | |
|---|---|---|---|
| Heart rate less than or equal to | 25 | BPM for | 30 seconds. |
| Document event: | ☑ Every | | 30 minutes. |
| | ☐ When heart rate decreases by | | 0 BPM. |
| Priority: | Low | | |

Asystole:
| | | | |
|---|---|---|---|
| Heart rate less than or equal to | 0 | BPM for | 7 seconds. |
| Document event: | ☑ Every | | 30 minutes. |
| Priority: | Urgent | | |

Pause:
| | | |
|---|---|---|
| Pause for | 3 | seconds. |
| Priority: | Medium | |

Atrial fibrillation:
| | | | |
|---|---|---|---|
| Heart rate greater than or equal to | 0 | BPM for | 5 minutes. |
| Priority: | Low | | |

[ Save ]  [ Cancel ]

FIG. 15

| Alarm name: | Ventricular fibrillation | | | | |
|---|---|---|---|---|---|
| | Heart rate greater than or equal to | 110 ▾ | BPM for | 15 ▾ | seconds. |
| | Document event: | ☑ Every | | 30 ▾ | minutes. |
| | Priority: | Urgent ▾ | | | |

| Alarm name: | High heart rate | | | | |
|---|---|---|---|---|---|
| | Heart rate greater than or equal to | 160 ▾ | BPM for | 5 ▾ | seconds. |
| | Document event: | ☑ Every | | 30 ▾ | minutes. |
| | | ☐ When heart rate increases by | | 0 ▾ | BPM. |
| | Priority: | Medium ▾ | | | |

| Alarm name: | Low heart rate | | | | |
|---|---|---|---|---|---|
| | Heart rate less than or equal to | 35 ▾ | BPM for | 5 ▾ | seconds. |
| | Document event: | ☑ Every | | 30 ▾ | minutes. |
| | | ☐ When heart rate decreases by | | 0 ▾ | BPM. |
| | Priority: | None ▾ | | | |

| Alarm name: | Very low heart rate | | | | |
|---|---|---|---|---|---|
| | Heart rate less than or equal to | 25 ▾ | BPM for | 30 ▾ | seconds. |
| | Document event: | ☑ Every | | 30 ▾ | minutes. |
| | | ☐ When heart rate changes by | | 0 ▾ | BPM. |
| | Priority: | Low ▾ | | | |

| Alarm name: | Asystole | | | | |
|---|---|---|---|---|---|
| | Heart rate less than or equal to | 0 ▾ | BPM for | 7 ▾ | seconds. |
| | Document event: | ☑ Every | | 30 ▾ | minutes. |
| | Priority: | Urgent ▾ | | | |

| Alarm name: | Pause | | |
|---|---|---|---|
| | Pause for | 3 ▾ | seconds. |
| | Priority: | Medium ▾ | |

| Alarm name: | Atrial fibrillation | | | | |
|---|---|---|---|---|---|
| | Heart rate greater than or equal to | 0 ▾ | BPM for | 5 ▾ | seconds. |
| | Priority: | Low ▾ | | | |

Custom alarms configuration:
☑ Enable custom alarm

| Alarm name: | Custom alarm | | | | |
|---|---|---|---|---|---|
| Heart rate | ⊙ <= ○ >= | 0 ▾ | BPM for | 5 ▾ | seconds. |
| Document event: | ☑ Every | | | 0 ▾ | minutes. |
| | ☑ When heart rate changes by | | | 0 ▾ | BPM. |
| Priority: | Urgent ▾ | | | | |

[ Save ]  [ Cancel ]

Kits

Kit serial number: [____] 182

Shipped from: [____] To: [____]
Received from: [____] To: [____]

Shipped Location: [All ▼] 184

[Search] [Reset]

| | | | | | | 186 |
|---|---|---|---|---|---|---|
| New Kit | | | | Receive Selected Kits | | Ship Selected Kits |

| Serial Number | Shipped Date | Shipping Location | Monitors | Communicators | Received Date | Modify |
|---|---|---|---|---|---|---|
| IPK001 | 01/07/2008 10:23 AM | Evergreen Medical Center | IPM002 IPM007 | 44444000080004 | 01/07/2008 10:29 AM | ☐ |
| IPK002 | 01/07/2008 10:23 AM | Evergreen Medical Center | IPM008 IPM006 | 44444000080009 | 01/07/2008 10:29 AM | ☐ |
| IPK004 | 01/07/2008 10:23 AM | Evergreen Medical Center | IPM005 IPM009 | 44444000080006 | | ☐ |
| IPK005 | 01/07/2008 10:23 AM | Overlake Medical Center | IPM004 IPM011 | 44444000080007 | | ☐ |
| IPK003 | 01/07/2008 10:23 AM | Overlake Medical Center | IPM014 IPM013 | 44444000080003 | | ☐ |
| IPK006 | 01/07/2008 10:23 AM | Overlake Medical Center | IPM003 IPM018 | 44444000080002 | | ☐ |
| IPK007 | | | IPM010 IPM017 | 44444000080008 | | Modify ☐ |
| IPK008 | | | IPM002 IPM001 | 44444000080005 | | Modify ☐ |
| IPK009 | 01/07/2008 10:30 AM | Evergreen Medical Center | IPM012 IPM016 | 44444000080010 | | ☐ |

Monitors

Serial number: [        ]    Search    Reset

| Monitor Id | Serial Number | Bluetooth Address | Modify |
|---|---|---|---|
| 1 | IPM001 | 95bftd001 | Modify |
| 2 | IPM002 | 95bftd002 | Modify |
| 3 | IPM003 | 95bftd003 | Modify |
| 4 | IPM004 | 95bftd004 | Modify |
| 5 | IPM005 | 95bftd005 | Modify |
| 6 | IPM006 | 95bftd006 | Modify |
| 7 | IPM007 | 95bftd007 | Modify |
| 8 | IPM008 | 95bftd008 | Modify |
| 9 | IPM009 | 95bftd009 | Modify |
| 10 | IPM010 | 95bftd010 | Modify |
| 11 | IPM011 | 95bftd011 | Modify |
| 12 | IPM012 | 95bftd012 | Modify |
| 13 | IPM013 | 95bftd013 | Modify |
| 14 | IPM014 | 95bftd014 | Modify |
| 15 | IPM015 | 95bftd015 | Modify |
| 16 | IPM016 | 95bftd016 | Modify |
| 17 | IPM017 | 95bftd017 | Modify |
| 18 | IPM018 | 95bftd018 | Modify |
| 19 | IPM019 | 95bftd019 | Modify |
| 20 | IPM020 | 95bftd020 | Modify |

[        ]    Add 1 2 3 4 5 6 7 8 9 10 11 12 13 14 15 ...

Monitor Usage

Monitor serial number: [          ]     Shipped from: [          ] 🔲 To: [          ] 🔲

Shipped Location: [All ▼]                Received from: [          ] 🔲 To: [          ] 🔲

[Search]  [Reset]

| Monitor Serial Number | Kit Serial Number | Shipped Date | Shipping Location | Received Date |
|---|---|---|---|---|
| IPM001 | IPK001 | 02/26/2008 02:53 PM | Eastside Heart Hospital | |
| IPM002 | IPK001 | 02/26/2008 02:53 PM | Eastside Heart Hospital | |
| IPM003 | IPK002 | 10/14/2007 12:00 PM | American Cardiac care | |
| IPM004 | IPK002 | 10/14/2007 12:00 PM | American Cardiac care | |
| IPM005 | IPK003 | 10/14/2007 12:00 PM | American Cardiac care | |
| IPM006 | IPK003 | 10/14/2007 12:00 PM | American Cardiac care | |
| IPM007 | IPK004 | 10/14/2007 12:00 PM | American Cardiac care | |
| IPM008 | IPK004 | 10/14/2007 12:00 PM | American Cardiac care | |
| IPM009 | IPK005 | 10/14/2007 12:00 PM | American Cardiac care | |
| IPM010 | IPK005 | 10/14/2007 12:00 PM | American Cardiac care | |
| IPM011 | IPK006 | 10/14/2007 12:00 PM | American Cardiac care | |
| IPM012 | IPK006 | 10/14/2007 12:00 PM | American Cardiac care | |
| IPM013 | IPK007 | 10/14/2007 12:00 PM | American Cardiac care | |
| IPM014 | IPK007 | 10/14/2007 12:00 PM | American Cardiac care | |
| IPM015 | IPK008 | 10/14/2007 12:00 PM | American Cardiac care | |
| IPM016 | IPK008 | 10/14/2007 12:00 PM | American Cardiac care | |
| IPM017 | IPK009 | 10/14/2007 12:00 PM | American Cardiac care | |
| IPM018 | IPK009 | 10/14/2007 12:00 PM | American Cardiac care | |
| IPM019 | IPK010 | 10/14/2007 12:00 PM | American Cardiac care | |
| IPM020 | IPK010 | 10/14/2007 12:00 PM | American Cardiac care | |

Communicators

IMEI: [____]  Phone number 1: [____]

[Search] [Reset]

| Id | IMEI | Bluetooth Address | Phone Number 1 | Phone Number 2 | Activation Code | Modify |
|---|---|---|---|---|---|---|
| 1 | 444440000800000 | 95ead0001 | 4940080000 | NULL | NULL | Modify |
| 2 | 444440000800001 | 95ead0002 | 4940080001 | NULL | NULL | Modify |
| 3 | 444440000800002 | 95ead0003 | 4940080002 | NULL | NULL | Modify |
| 4 | 444440000800003 | 95ead0004 | 4940080003 | NULL | NULL | Modify |
| 5 | 444440000800004 | 95ead0005 | 4940080004 | NULL | NULL | Modify |
| 6 | 444440000800005 | 95ead0006 | 4940080005 | NULL | NULL | Modify |
| 7 | 444440000800006 | 95ead0007 | 4940080006 | NULL | NULL | Modify |
| 8 | 444440000800007 | 95ead0008 | 4940080007 | NULL | NULL | Modify |
| 9 | 444440000800008 | 95ead0009 | 4940080008 | NULL | NULL | Modify |
| 10 | 444440000800009 | 95ead00010 | 4940080009 | NULL | NULL | Modify |
| 11 | 444440000800010 | 95ead00011 | 4940080010 | NULL | NULL | Modify |
| 12 | 444440000800011 | 95ead00012 | 4940080011 | NULL | NULL | Modify |
| 13 | 444440000800012 | 95ead00013 | 4940080012 | NULL | NULL | Modify |
| 14 | 444440000800013 | 95ead00014 | 4940080013 | NULL | NULL | Modify |
| 15 | 444440000800014 | 95ead00015 | 4940080014 | NULL | NULL | Modify |
| 16 | 444440000800015 | 95ead00016 | 4940080015 | NULL | NULL | Modify |
| 17 | 444440000800016 | 95ead00017 | 4940080016 | NULL | NULL | Modify |
| 18 | 444440000800017 | 95ead00018 | 4940080017 | NULL | NULL | Modify |
| 19 | 444440000800018 | 95ead00019 | 4940080018 | NULL | NULL | Modify |
| 20 | 444440000800019 | 95ead00020 | 4940080019 | NULL | NULL | Modify |

[____] [____] [____] [____] Add 1 2 3 4 5 6 7 8 9 10 11 12 13 14 15 ...

Communicator Usage

Communicator IMEI: [ ]  Shipped from: [ ] To: [ ]

Shipped Location: [All ▾]  Received from: [ ] To: [ ]

[Search] [Reset]

| IMEI | Phone Number 1 | Kit Serial Number | Shipped Date | Shipping Location | Returned Date |
|---|---|---|---|---|---|
| 444400008000000 | 4940080000 | IPK001 | 02/25/2008 02:53 PM | Eastside Heart Hospital | |
| 444400008000001 | 4940080001 | IPK002 | 10/14/2007 12:00 PM | American Cardiac care | |
| 444400008000002 | 4940080002 | IPK003 | 10/14/2007 12:00 PM | American Cardiac care | |
| 444400008000003 | 4940080003 | IPK004 | 10/14/2007 12:00 PM | American Cardiac care | |
| 444400008000004 | 4940080004 | IPK005 | 10/14/2007 12:00 PM | American Cardiac care | |
| 444400008000005 | 4940080005 | IPK006 | 10/14/2007 12:00 PM | American Cardiac care | |
| 444400008000006 | 4940080006 | IPK007 | 10/14/2007 12:00 PM | American Cardiac care | |
| 444400008000007 | 4940080007 | IPK008 | 10/14/2007 12:00 PM | American Cardiac care | |
| 444400008000008 | 4940080008 | IPK009 | 10/14/2007 12:00 PM | American Cardiac care | |
| 444400008000009 | 4940080009 | IPK010 | 10/14/2007 12:00 PM | American Cardiac care | |
| 444400008000010 | 4940080010 | IPK011 | 10/14/2007 12:00 PM | American Cardiac care | |
| 444400008000011 | 4940080011 | IPK012 | 10/14/2007 12:00 PM | American Cardiac care | |
| 444400008000012 | 4940080012 | IPK013 | 10/14/2007 12:00 PM | American Cardiac care | |
| 444400008000013 | 4940080013 | IPK014 | 10/14/2007 12:00 PM | American Cardiac care | |
| 444400008000014 | 4940080014 | IPK015 | 10/14/2007 12:00 PM | American Cardiac care | |
| 444400008000015 | 4940080015 | IPK016 | 10/14/2007 12:00 PM | American Cardiac care | |
| 444400008000016 | 4940080016 | IPK017 | 10/14/2007 12:00 PM | American Cardiac care | |
| 444400008000017 | 4940080017 | IPK018 | 10/14/2007 12:00 PM | American Cardiac care | |
| 444400008000018 | 4940080018 | IPK019 | 10/14/2007 12:00 PM | American Cardiac care | |
| 444400008000019 | 4940080019 | IPK020 | 10/14/2007 12:00 PM | American Cardiac care | |

Patient Nightly Reminder Setup for Linda Williams

Procedure details:

Procedure Id: 2  Status: In procedure
Start date: 1/7/2008 10:31:00 AM  End date: 2/6/2008 10:31:00 AM Nightly charging reminder schedule:

Change history: 1/7/2008 10:32:04 AM ⌄
Changed by: Monitoring Center

Patient will be reminded at the following times (hh:mm AM/PM) to charge the monitor and communicator.

Monday     09:00 PM
Tuesday    09:00 PM
Wednesday  09:00 PM
Thursday   09:00 PM
Friday     09:00 PM
Saturday   09:00 PM
Sunday     09:00 PM

[ Modify ]   [ Procedure History ]

FIG. 24

Procedure Reports Delivery Setup

Patient Name : Linda Wilson

Procedure details:

Procedure Id: 10
Start date: 2/8/2008 8:49:00 AM
Status: In procedure
End date: 3/9/2008 8:49:00 AM Reports delivery:

Change history: 2/12/2008 12:34:58 PM ▽
Changed by: Monitoring Center
Delivery time: 06:00 AM ▽  Pacific time ▽
Email delivery: ☐ Clinician  ☐ Physician
Fax delivery: ☑ Clinician  ☑ Physician
Mail delivery: ☑ Clinician  ☐ Physician

[Modify]  [Procedure History]

User Activity Details - Monitoring Center

Active Details:

| | | | |
|---|---|---|---|
| Account status: | Active | Last login date: | 01/07/2008 11:09:46 AM |
| Lockout: | Unlocked | Last lockout date: | |
| Last password change date: | 01/07/2008 10:08:29 AM | | |
| Failed password attempts: | 0 | Failed password attempts start date: | |
| Failed password answer attempts: | 0 | Failed password answer attempt start: | |

Activity Log - Number of Logins:

- In Past 24 hours: 7
- In Past 7 days: 9
- In Past 30 days: 9
- Total Logins: 9

262

Clear Activity History

| IP Address | Login Date | Logout Date |
|---|---|---|
| 127.0.0.1 | 01/07/2008 11:09:46 AM | |
| 127.0.0.1 | 01/07/2008 10:44:43 AM | |
| 127.0.0.1 | 01/07/2008 10:31:17 AM | 01/07/2008 10:32:28 AM |
| 127.0.0.1 | 01/07/2008 10:25:53 AM | |
| 127.0.0.1 | 01/07/2008 10:10:54 AM | 01/07/2008 10:11:09 AM |
| 127.0.0.1 | 01/07/2008 09:39:50 AM | 01/07/2008 10:09:45 AM |
| 127.0.0.1 | 01/07/2008 09:31:07 AM | |
| 127.0.0.1 | 01/07/2008 03:49:32 PM | |
| 127.0.0.1 | 01/07/2008 03:36:13 PM | |

Back to Search

Monitoring Center Originated Logs

| Site: | Select site ▾ | First Name: | | Last Name: | |
|---|---|---|---|---|---|
| Physician: | Select physician ▾ | Patient Id: | | Procedure Id: | |

[ Search ]  [ Reset ]

| Physician | Patient | Patient Id | Procedure Id | Procedure Start Date | Procedure End Date | Logs |
|---|---|---|---|---|---|---|
| Matt Kimmons | James V Smith | 1 | 1 | 01/07/2008 10:24 AM | 01/07/2008 10:28 AM | View |
| Abigail Arthur | Linda I Williams | 3 | 2 | 01/07/2008 10:31 AM | 02/06/2008 10:31 AM | View |

— 272

Log for James V Smith - Procedure started on 1/7/2008 10:24:00 AM

Entry time: 01/07/2008 11:23:07 AM
Event time: 01/07/2008 11:23 AM 🗓
Event Category: Device issue ▾
Alert Notification Id:

Notes:

[                    ]
1000 characters left

[ Create Log ]  [ Cancel ]

— 274

New Log

| Entry Time | Event Time | Event Category | Notification Id | Notes |
|---|---|---|---|---|
| 01/07/2008 10:45 AM | 01/07/2008 10:45 AM | Other symptoms | | Experienced mild palpitations and dizziness. |
| 01/07/2008 10:45 AM | 01/07/2008 10:45 AM | Device issue | | Phone got run over by car. |

FIG. 27

Status Notifications

First Name: [ ]  Last Name: [ ]  Notification Event: [Mode change / Good Contact / Alarm HR Low / Bad Contact]  Severity: [All]
Patient Id: [ ]  Procedure Id: [ ]  Received Before: [ ]
Communicator ID: [ ]  Use Ctrl+Click to select multiple events.  Received After: [ ]

[Search]  [Reset]

[Acknowledge Selected]  [View All]  Severity: Urgent High Medium Low None

| | Event Type | Event Time | Received Time | Event Details | ECG | Audio |
|---|---|---|---|---|---|---|
| ☐ | alarmHRLo | 8/1/2006 4:14:24 AM | 12/18/2006 6:52:02 PM | 2 | | |
| ☐ | modeChange | 3/7/1993 12:45:18 PM | 12/20/2006 11:24:27 AM | 223 | | |
| ☐ | modeChange | 12/20/2006 6:22:57 PM | 12/20/2006 11:24:35 AM | 224 | | |
| ☐ | modeChange | 12/20/2006 6:23:32 PM | 12/20/2006 11:24:42 AM | 225 | | |
| ☑ | modeChange | 12/20/2006 6:54:44 PM | 12/20/2006 11:55:00 AM | 229 | | |
| ☑ | modeChange | 12/20/2006 6:55:17 PM | 12/20/2006 11:55:24 AM | 230 | | |
| ☐ | modeChange | 3/7/1993 12:45:18 PM | 12/20/2006 1:01:41 PM | 254 | | |
| ☐ | modeChange | 12/20/2006 8:00:48 PM | 12/20/2006 1:01:49 PM | 255 | | |
| ☐ | modeChange | 12/20/2006 8:05:31 PM | 12/20/2006 1:10:22 PM | 257 | | |
| ☐ | modeChange | 12/20/2006 8:11:57 PM | 12/20/2006 1:12:09 PM | 258 | | |
| ☐ | modeChange | 12/20/2006 8:15:43 PM | 12/20/2006 1:15:52 PM | 259 | | |
| ☐ | modeChange | 12/20/2006 8:15:43 PM | 12/20/2006 1:15:57 PM | 260 | | |
| ☐ | modeChange | 12/20/2006 8:16:12 PM | 12/20/2006 1:16:20 PM | 261 | | |
| ☐ | modeChange | 12/20/2006 8:16:34 PM | 12/20/2006 1:16:44 PM | 262 | | |
| ☐ | modeChange | 3/7/1993 12:45:18 PM | 12/20/2006 1:53:52 PM | 263 | | |

ECG MONITORING SYTSTEM WITH DOCKING STATION

This application is a continuation in part application of pending international application no. PCT/IB2006/054019, filed Oct. 30, 2006, which claims the benefit of U.S. provisional application Ser. No. 60/741,492, filed Nov. 30, 2005.

This invention relates to ECG monitoring systems and, in particular, to the continuous ECG monitoring of patients in an outpatient setting.

Numerous patients have a demonstrated need for continuous cardiac monitoring over an extended period of time. This patient population includes those who may have arrhythmias such as atrial fibrillation, atrial flutter, and other supraventricular tachycardias, and atrial or ventricular ectopy, brady arrhythmias, intermittent bundle branch block, and arrhythmias associated with conditions such as hyperthyroidism or chronic lung disease. Other patients may exhibit symptoms that may be due to cardiac arrhythmias such as dizziness or lightheadedness, syncope, or dyspnea. Other patients may experience palpitations for which it is desirable to correlate patient rhythm with symptoms. Other patient conditions may need to be monitored for cardiac effects of drugs, in situations where the arrhythmic effects of drugs or the effects of drugs to suppress arrhythmias should be monitored. For drugs with known arrhythmic effects, possible lengthening of the QT interval should be monitored. Patients who have diagnosed sleep disordered breathing such as sleep apnea, have suffered a stroke or transient ischemia, or are recovering from cardiac surgery may often benefit from continuous cardiac monitoring.

Several monitoring devices are presently used for some of these conditions. Holter monitors are used to continuously record a patient's ECG waveform over a period of time such as a 24-hour period. However, the data recorded by a Holter monitor is only known and can be analyzed after the recording period is over. Immediate analysis of the ECG is not possible when the ECG data is only recorded and not immediately reported. Also, many patients feel constrained from engaging in normal activities when wearing a Holter monitor and its many lead wires and electrodes, and often object to the discomfort and inconvenience of these monitors.

Another monitoring device in present use is the loop or event monitor. A loop monitor records data in a continuous loop recording. When the loop is full, the loop monitor will overwrite previously recorded data. A loop monitor is therefore ineffective as a full disclosure recorder for an extended period of time since data can be lost. With an event monitor the patient is attached to numerous electrodes and wires so that the monitor can be activated by the patient whenever the patient feels symptomatic. When the patient feels pain or discomfort the patient activates the monitor to record the ECG at the time of the symptom. Some monitoring systems also enable the ECG data to be transmitted to a local base station which relays the ECG data by phone to a diagnostic center where it can be promptly scrutinized for arrhythmias. However this constrains the normal daily activities of the patient, as the patient must continually stay within range of the local base station.

Still other monitors have a recorder which is auto-triggered by a cardiac event to record the ECG at the time of the event. The patient will then connect the monitor to a telephone line modem to transfer the ECG data to a monitoring center for review. These systems pose numerous problems. One is that a patient mistake in connecting the monitor to the telephone equipment or operating the equipment can result in a loss of uploaded data. Another problem is that a cardiac event such as syncope can leave the patient unconscious or disoriented and unable to conduct the upload process correctly or, in some cases, at all. Moreover, if the cardiac event occurs while the patient is traveling in a car, considerable time may pass before the patient returns to the location of the uploading equipment and is able to perform the data upload process.

Accordingly it would be desirable for a cardiac monitoring system to overcome the shortcomings of these devices. Such a monitoring system would continuously record the patient's ECG waveforms, analyze the ECG for arrhythmias in real time, and send ECG data to a diagnosing clinician whenever a possibly significant arrhythmia is detected. The system would also be operable by the patient to record a symptomatic event, preferably with an oral description of the event, and would then automatically send the description of the symptom and the associated ECG data to a clinician or monitoring center for review. The monitoring system would desirably be very comfortable and convenient for the patient to use without disrupting the patient's normal daily activities.

In accordance with the principles of the present invention, an ECG monitoring system is provided which is completely wireless for patient comfort and convenience. A small monitor adhesively attaches to the chest of a patient. The monitor continuously records and analyzes the patient's ECG. If a suspected arrhythmia is detected, a strip of ECG data is immediately sent to a cellphone and forwarded on to a monitoring center for clinical review. The patient can also make a voice record of a symptomatic event with the cellphone, which promptly sends the voice record and a concurrent ECG strip to the monitoring center. The monitor is placed in a charging dock each day for recharging while the patient wears a previously charged monitor. While it is docked the monitor downloads its archive of continuously recorded ECG data to the cellphone, which forwards the data on to the monitoring center for analysis.

In the drawings:

FIG. 15 illustrates a screen display of a setup template for the configuration and alert limits of an ECG monitor of the present invention.

FIG. 16 illustrates a screen display to set up procedure configuration and alarm limits for an ECG monitor of the present invention, showing a custom alarm.

FIG. 17 illustrates a screen display used to associate the components of an ECG monitoring kit of the present invention.

FIG. 18 illustrates a screen display used to track the disposition of ECG monitoring kits of the present invention.

FIG. 19 illustrates a screen display used to track ECG monitors and their Bluetooth addresses in accordance with the present invention.

FIG. 20 illustrates a screen display used to track ECG monitor usage in accordance with the principles of the present invention.

FIG. 21 illustrates a screen display used to track cellphone handsets, their phone numbers and Bluetooth addresses in accordance with the present invention.

FIG. 22 illustrates a screen display used to track ECG handset usage in accordance with the present invention.

FIG. 24 illustrates a setup screen used to program the generation of reminders for a patient to recharge a monitor and cellphone handset of an ECG monitoring system of the present invention.

FIG. 25 illustrates a screen display used by a monitoring center to record a physician's requirements for reports during use of an ECG monitoring system of the present invention.

FIG. 26 illustrates a screen display to track account activity during use of an ECG monitoring system of the present invention.

FIG. 27 illustrates a screen display of the patient communication log for an ECG monitoring procedure conducted in accordance with the principles of the present invention.

FIG. 30 illustrates a screen display of status notifications received from an ECG monitor of the present invention.

Figure 1:
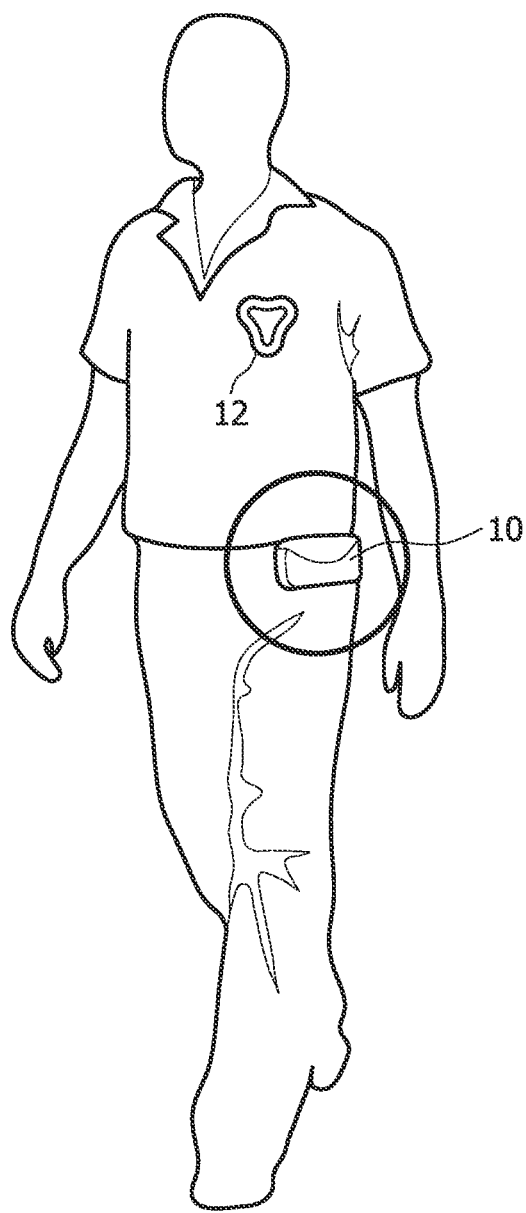
FIG. 1 illustrates a patient wearing an ECG monitoring system of the present invention.

FIG. 1 illustrates the significant patient comfort and ease of use of a wireless ECG monitoring system constructed in accordance with the principles of the present invention. The man in the drawing of FIG. 1 is going about his normal daily activities, unbothered and unhindered by the continuous ECG monitoring system he is wearing. This is because the ECG monitoring system he is wearing is thin, lightweight, and comfortable to wear. In the main, it is because the ECG monitoring system has no wires draped about the man's body. There are no wires from the monitor to electrodes on other areas of the body, no wires connecting the monitor to a communicator, and no wires connecting a communicator to a communication network. The ECG monitoring system is completely wireless. To a casual observer it would only appear that the man is wearing a cellphone in a carrying case 10 which is circled on the hip of the man. Shown on the chest of the man is a wireless ECG monitor 12 of the present invention. Although the location of the ECG monitor 12 is shown in FIG. 1, in fact the monitor would be unseen by an observer because it would be under the man's shirt. With a diameter of less than 2.5", a thickness of 0.5", and a weight of less than an ounce, the monitor would be virtually invisible under the man's clothing. As the man goes about his daily activities, the ECG monitor 12 continuously monitors, analyzes, and records the ECG of each heartbeat. If an arrhythmia is detected by the monitor, an alert and an ECG strip are wirelessly sent to the cellphone handset in the carrying case 10. The cellphone handset silently calls a monitoring center which may be hundreds or thousands of miles away and relays the alert and ECG strip to the monitoring center. At the monitoring center this cardiac information is promptly reviewed by a medical specialist and any necessary action taken or report made to the patient's physician. The patient's cardiac function is monitored in this way for 24 hours a day for typically several weeks (e.g., 10-30 days), providing an archive of ECG information and a level of arrhythmia protection not otherwise available on an outpatient basis.

Figure 2:
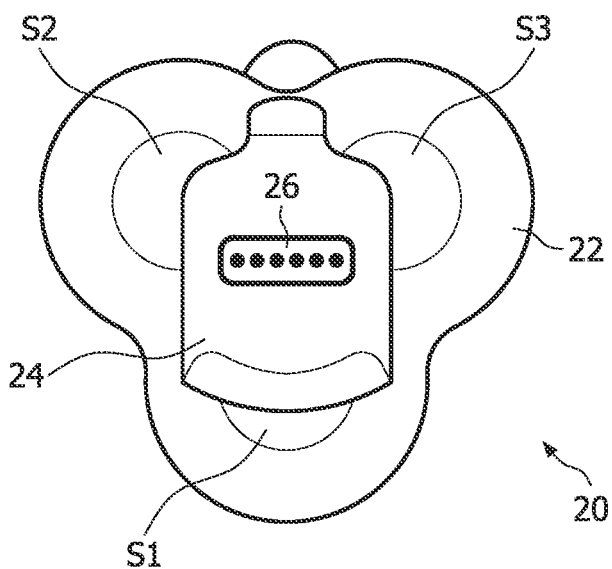
FIG. 2 illustrates an electrode patch which adhesively attaches to the chest of a patient and holds an ECG monitor.
Figure 4:
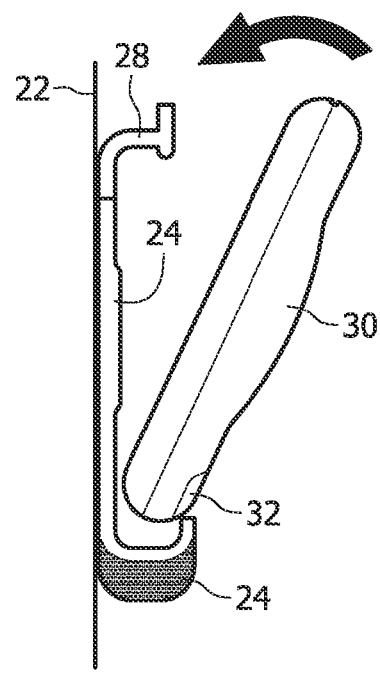
FIG. 4 illustrates how an ECG monitor of FIG. 3 snaps into the electrode patch of FIG. 2.

FIG. 2 illustrates an electrode patch 20 suitable for use with a wireless ECG monitor of the present invention. This patch and variations thereof are described in detail in the parent application which is published as international publication number WO2007/063436, the contents of which are incorporated herein by reference. FIG. 2 is a view of the outward-facing side of the patch 20. The patch is formed of a flexible substrate 22. On the back (patient-facing side) of the patch are four hydrogel electrode pads s1, s2 and s3 and a central electrode pad not visible in this drawing. The central electrode pad is a reference or RLD electrode, so named for its correspondence to the "right leg drive" reference electrode of a standard ECG set. The rest of the patient-facing side of the patch 20 is covered by a biocompatible adhesive which securely attaches the patch to the chest of a patient. Electrical signals received at the three electrode pads s1, s2 and s3 are coupled to electrical contacts on the outward-facing side of the patch by a flex circuit layer as described in the parent application and the signals so provided are used to form three ECG lead vectors as described below. In the center of the patch on the outward-facing side is a plastic clip 24 with curved lips at the top and bottom into which an ECG monitor may be snapped and retained as shown in FIG. 4. In the center of the clip 24 is a row of elastomeric contacts 26 by which the electrical signals received by the electrode pads s1, s2 and s3 are coupled to the ECG monitor, and a reference signal produced by the ECG monitor is coupled to the RLD electrode for the sensing of loose electrodes and reduction of common mode noise.

Figure 3A:
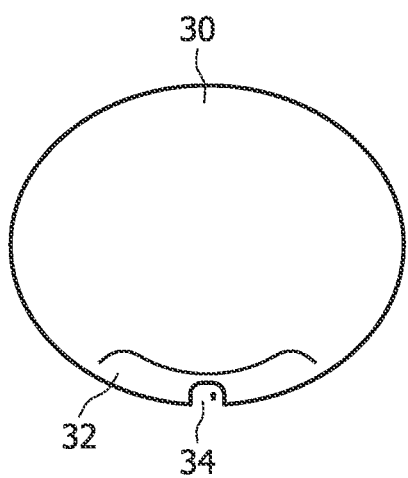
FIGS. 3a and 3b illustrate front and back views of ECG monitors of the present invention which clip into the patch of FIG. 2.
Figure 3B:
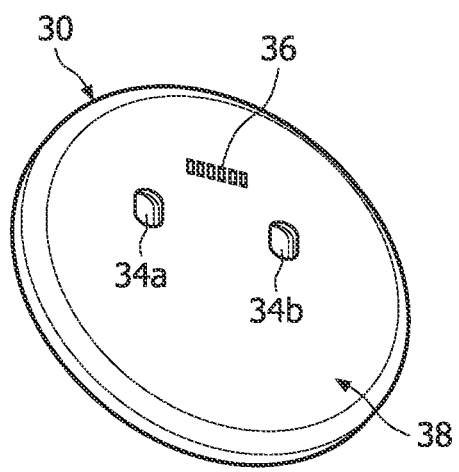

FIG. 3a is a plan view of the outward-facing front side of an ECG monitor 30 constructed in accordance with the principles of the present invention. The ECG monitor 30 is enclosed in a plastic clamshell case which is ultrasonically welded closed or sealed closed with an adhesive or solvent. On the back 38 of the case as shown in the example of FIG. 3b is a row of electrical contacts 36 which are inserted in and thermally sealed flush with the case surface. In a constructed embodiment there are three rows of electrical contacts 36. One of these rows makes connection with the elastomeric contacts 26 of the clip 24 and couples the ECG signals into the monitor and applies a small signal to the reference electrode. The other two rows engage matching rows of contacts in a charging dock when the monitor 30 is being recharged as described below. The monitor in this example has no external controls or displays and no on/off switch, only electrical contacts 36 on the back of the case. In a constructed embodiment the ECG monitor measures 2.4" wide by 1.9" high by 0.5" thick, and weighs 0.9 ounces. Since the case is sealed closed around its periphery and the contacts on the back are fully sealed, the monitor can be worn in the shower while posing no hazard to either the patient or the monitor. As the case is closed permanently in this embodiment, replacement of the internal battery or components is not possible in this design. If the monitor fails to operate properly or the battery is no longer capable of holding a sufficient charge, it is disposed of properly.

The plastic case is keyed on the bottom with an indentation 32 that matches the shape of the bottom of the clip 24 of the electrode patch 20. A notch 34 is also formed in the bottom of the case, which matches a projection inside the bottom of the clip. The example of FIG. 3b has two indentations 34a and 34b for keying to matching projections of a patch clip 24. This keying mandates that the ECG monitor 30 can only be snapped into the clip 24 in one orientation. FIG. 4 is a side view showing the monitor 30 being snapped into the clip 24. The bottom of the monitor of FIG. 3a is inserted into the clip first with the keying 32,34 of the bottom of the monitor engaging the matching shape of the bottom of the clip. The top of the monitor is then tilted back to the top of the clip as indicated by the arrow in FIG. 4, and the top of the monitor snaps under the top 28 of the clip 24. As the monitor snaps into place, providing a tactile indication to the patient that the monitor is in place, the contacts 36 on the back of the monitor are aligned with and engage the row of contacts 26 of the clip. The monitor is now in position to monitor the ECG signals of the patient, which commences at once as the monitor senses this engagement, terminates its "sleep" mode, and powers up to full operational capability.

Figure 5:
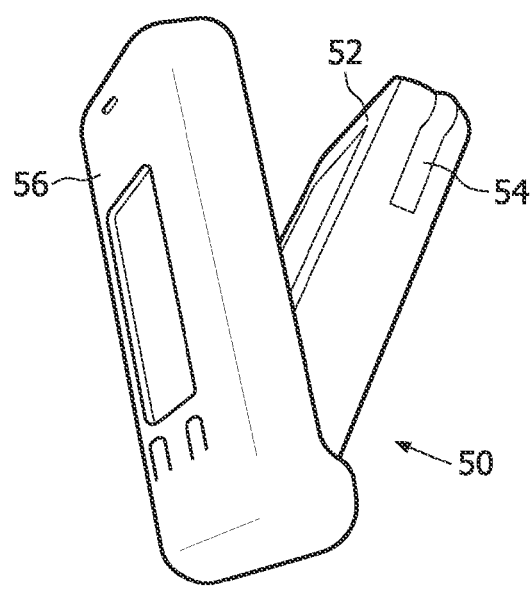
FIG. 5 illustrates the cellphone handset of an ECG monitoring system of the present invention with its cover.
Figure 7:
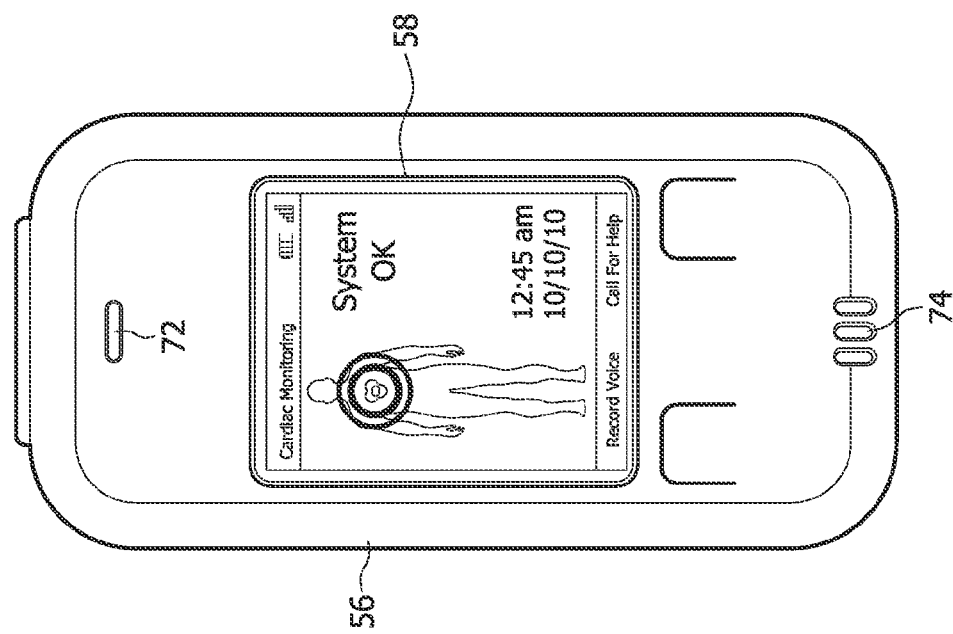
FIG. 7 is a plan view of the front of the cellphone handset of FIGS. 5 and 6 when the handset is in communication with a monitor.
Figure 6:
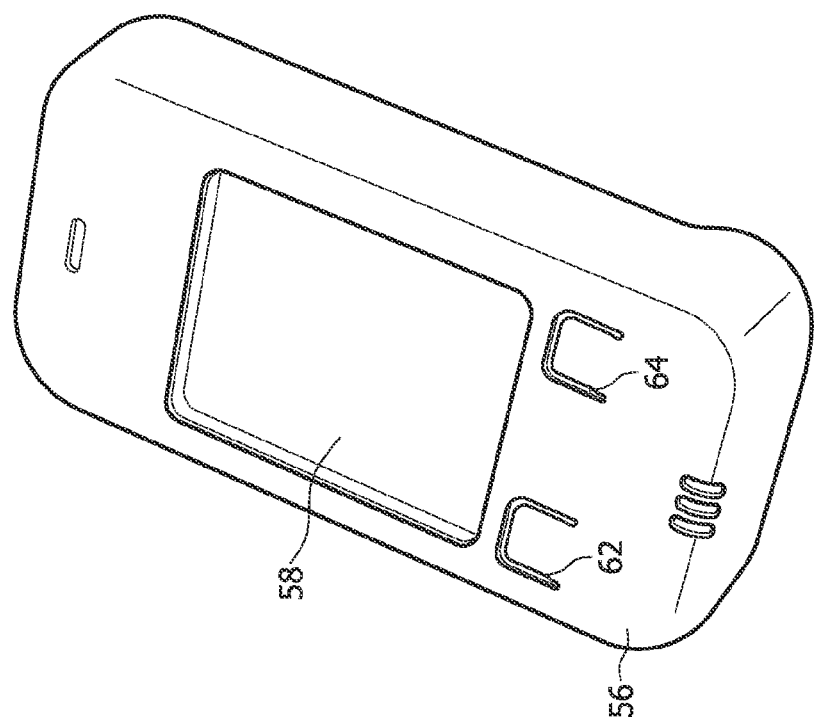
FIG. 6 illustrates the cellphone handset of FIG. 5 with the cover snapped onto the cellphone.

FIGS. 5-7 illustrate a cellphone handset 50 suitable for use with the ECG monitor 30 of FIG. 3. The cellphone handset 50 includes a standard commercially available "smart phone" cellphone 52 over which is placed a plastic cover 56, which snaps into place. The cover 56 functions to cover up most of the keys of a standard cellphone and restricts the patient to use of only a few buttons necessary for the ECG monitoring procedure. The cover thereby turns an often complex commercial cellphone into a communicator which is simple for the patient to understand and use. FIG. 5 shows the cellphone 52 being placed in the cover 56. The on/off button 54 is shown located on the side of the cellphone 52 and the cellphone 52 is turned on before the cover is snapped on. As FIG. 6, shows, the cover 56 has a hole on the front the size of the cellphone screen so that the screen 58 of the cellphone 52 can be observed through the hole in the cover. The cover also has two partial cutouts 62 and 64 on the front. These cutouts 62,64 can be depressed by the patient as buttons to operate the two underlying keys of the cellphone keypad. In other implementations the cover may cover most of the keys of the cellphone and leave only a few keys uncovered and available for use. The cutouts or uncovered keys are operated as "soft keys", with the functions affected by key depression at any moment shown on the cellphone screen 58 at the bottom of the screen and just above each cutout. Depending on the operation of the monitoring system and the actions of the patient, these functions will change as described below. FIG. 7 is a front view of the covered cellphone handset showing the screen 58, the buttons below the screen, a small hole 72 at the top of the cover through which the patient can listen to the earphone of the cellphone, and three small holes 74 at the bottom of the cover 56, into which the patient can speak when recording a message or conversing with the monitoring center as discussed below. When the cellphone 52 is turned on and the cover 56 is in place, there are only two buttons, 62 and 64, which can be operated by the patient in this embodiment.

A significant advantage of this commercial cellphone with cover implementation is that the monitoring system can be quickly and inexpensively adapted to new cellphone technology. As new cellphone models are introduced and older ones become obsolete, a new cellphone model can be used by redesigning the cover to fit the new model and producing the new cover in inexpensive high volumes as an injection molded part, for instance. The effort and cost to do so is far less than that required to design and produce a custom cellphone communicator, which would not keep up with technological changes and would be expensive in low volumes. The inventive approach of adapting a new cover to new commercial cellphone models enables the monitoring system designer to take advantage of the low cost of high volume commercial cellphones and avoid the need for an expensive and technically limiting custom communicator.

In other embodiments it may desirable to provide additional buttons or button functions for the patient to use. For instance, an information button labeled "i" can be provided for use by a patient when he has a question about the current state of the monitor or a message. If a message appears on the screen which the patient does not understand, the patient presses the "i" button, and the cellphone handset will provide information about the current state of the monitor or message on the display 58. Such information is context driven as determined by the current state or status of the system. The information can be provided as text on the display 58 of the handset, or as a voice prompt which is played and articulates the information audibly. Another button which may be desirable is a "911" button which calls the 911 emergency response service when pressed. Another button which may be useful in a particular embodiment is a "Physician" button which automatically dials the phone number of the patient's physician when pressed.

Figure 8C:
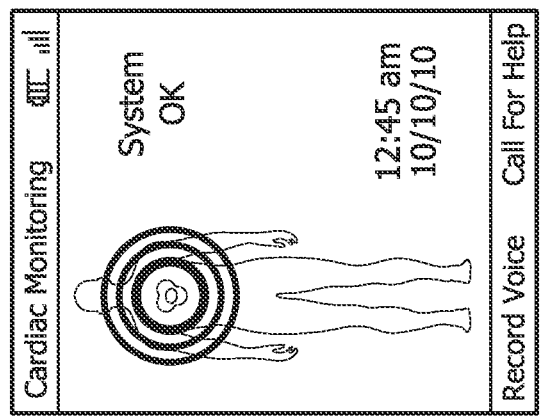
FIGS. 8a-8i illustrate some of the screen displays of a typical cellphone handset of an ECG monitoring system of the present invention.
Figure 8B:
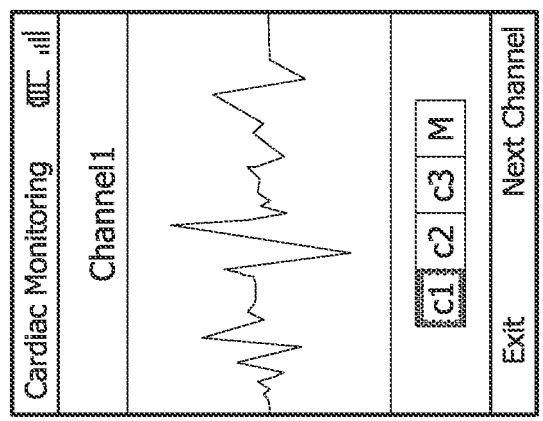
Figure 8A:
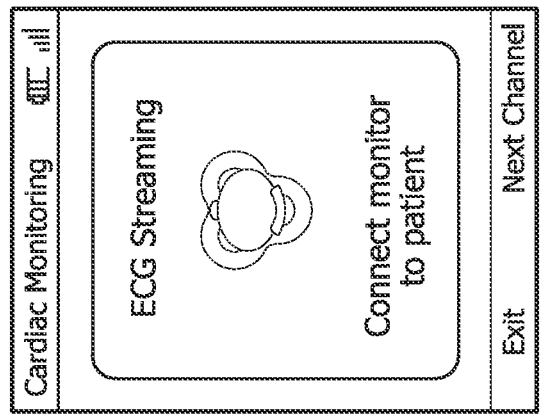

FIGS. 8a-8i are examples of displays shown on the screen of the cellphone handset during use of the ECG monitoring system of the present invention. FIG. 8a shows the screen display when the monitor and handset are in the "ECG streaming" mode. This is a mode which can be initiated by the physician when the patient is first set up with the monitor. During setup, the physician will place the electrode patch and monitor at various locations on the patient's chest, looking for a number of locations where a good ECG signal can be received. In a constructed embodiment this is done by peeling a portion of the release liner to uncover the electrode gel without uncovering the patch adhesive as explained in international patent application number IB2007/054879 (Cross et al.) In order to gauge the effectiveness of a given location, the physician will type in a certain key combination on the cellphone keypad when the cover 56 is removed from the cellphone. The key combination switches the cellphone operation to the ECG streaming mode. If the ECG monitor and electrode patch are not both attached to the patient at the time this mode is entered, the screen display of FIG. 8a is shown, with the instruction to connect the monitor to the patient. When the monitor 30 is in place on the patient, the patient's ECG waveform is streamed to the display and shown in real time as a function of time and amplitude as it is received from the patient, as shown in FIG. 8b. The ECG monitor sends four channels of data to the monitoring center, three channels of ECG lead data identified in FIG. 8b as c1, c2, and c3, and a channel M of motion information. In other embodiments other channels of data may be provided such as a reference signal channel. By depressing the right button 64 the physician can toggle through the display of all four channels of information. After the physician has found the desired number of electrode patch locations and has verified operation of the ECG monitor 30 and cellphone handset 50 in the ECG streaming mode, the left button 62 is depressed to exit the ECG streaming mode. The "System OK" display of FIG. 8c should then appear on the screen. This screen appears when the following conditions are met: the ECG monitor 30 is communicating with the cellphone handset 50; the ECG monitor and handset system software are both functioning properly; the contact quality of the electrode patch 20 to the skin of the patient is acceptable; and the most recently conducted monitor self-test was successful. Thus, the display of FIG. 8c indicates that the ECG monitor 30 and patch 20 are properly applied to the patient and that the ECG monitor and the cellphone handset 50 are operating properly. In other implementations it may be desirable to display a message or graphic indicating that communication with the ECG monitor is satisfactory. Another alternative is for the cellphone handset to selectively produce a tone when communication with the monitor is satisfactory, such as a beep in synchronism with received R-wave information. At the bottom of the display of FIG. 8c are the button labels seen on the screen above buttons 62 and 64 when the system is in its normal monitoring operation. The left button 62 is used to "Record Voice", and the right button 64 is used to "Call For Help."

Figure 8F:
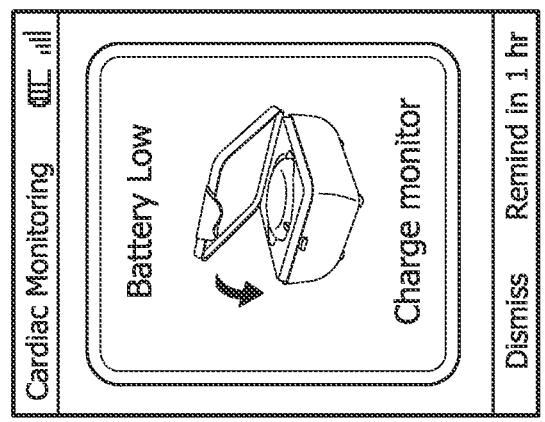
Figure 8E:
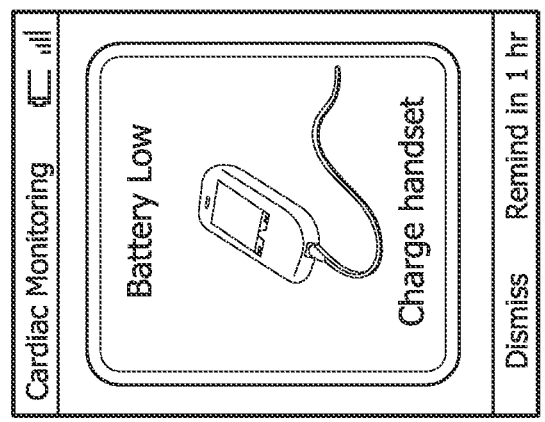
Figure 8D:
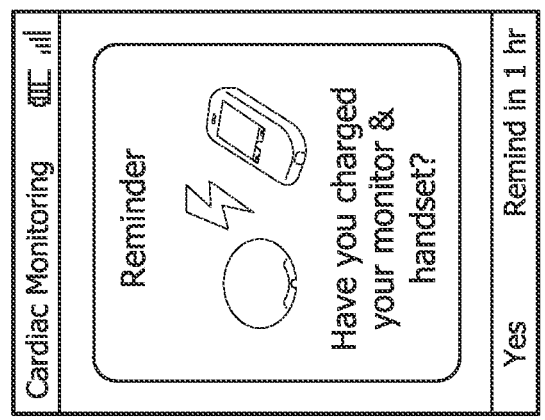
Figure 8I:
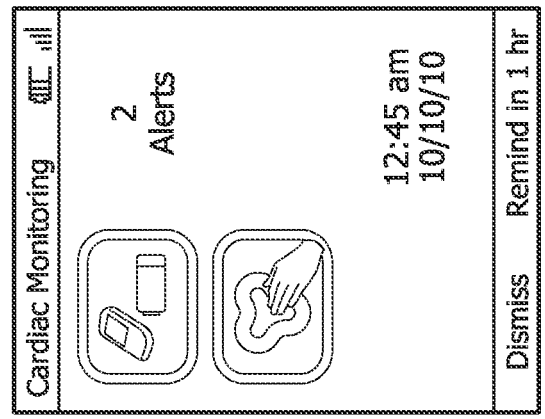
Figure 8H:
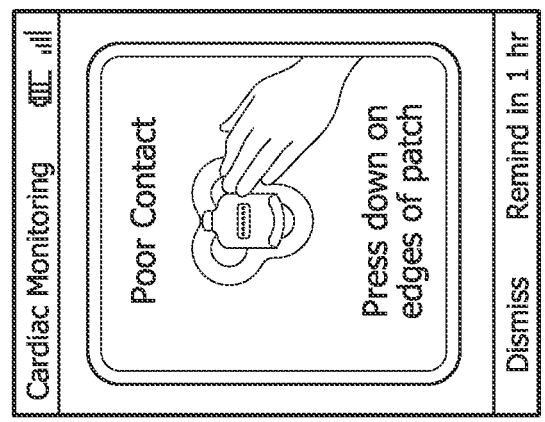
Figure 8G:
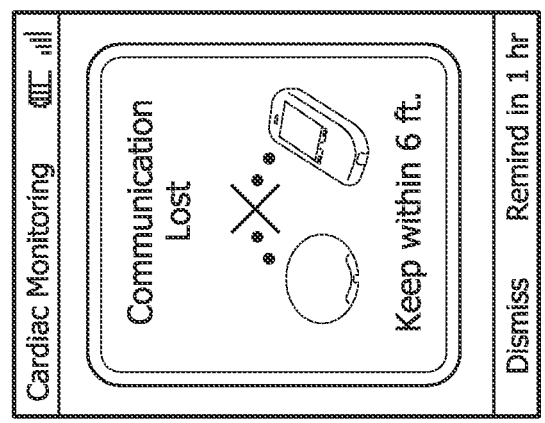

FIG. 8d shows a reminder display, reminding a patient at the end of the day that the monitor and handset need to be charged. As described below, this reminder screen will appear at a pre-programmed time each day if the patient has not begun to recharge the monitor and handset. FIG. 8e is a display which appears when the battery charge of the cellphone handset is detected to be low. FIG. 8f is a display that notifies the patient that the battery charge of the monitor 30 is low. FIG. 8g is a display that appears on the handset screen when the cellphone handset 50 loses communication with the ECG monitor 30. In the constructed embodiment the ECG monitor 30 and the cellphone handset 50 communicate with each other via wireless Bluetooth radio. The patient is advised to keep the cellphone handset and ECG monitor within six feet of each other to maintain the Bluetooth wireless link. If the patient sets the handset down and walks away from it, the display of FIG. 8g will appear when Bluetooth communication is broken. It is for this reason that the patient is advised to wear the cellphone handset in a carrying case on the waist, which maintains the Bluetooth link continuously. FIG. 8h is the display shown on the screen when the ECG monitor 30 detects poor contact with the skin of the patient. The patient is advised to press down on the edges of the electrode patch 20 to more securely adhere it to the skin.

For all of these alert conditions, the patient can depress the left button 62 to dismiss the alert from the screen (FIG. 8d). Depressing the right button 64 will cause the reminder to reappear in an hour. Alerts which have been dismissed will remain displayed on the screen as small icons as shown in FIG. 8i, until the patient takes the requested action or addresses the notified condition.

Whenever an alert appears on the screen, the cellphone handset concurrently sounds a tone to audibly inform the patient that a notification has appeared. The attention of the patient is thereby directed to the notification. Simultaneously with or instead of the display notifications, voice prompts stored on the cellphone handset can be played through the speakerphone of the handset. For example, instead of or in addition to a display showing "Poor Contact" and "Press down on edges of patch," the patient can hear a voice saying that the contact between the patch and the body has become poor and the patient should press down in the center of the patch and around its edges to reattach the patch to the body properly.

Figure 9:
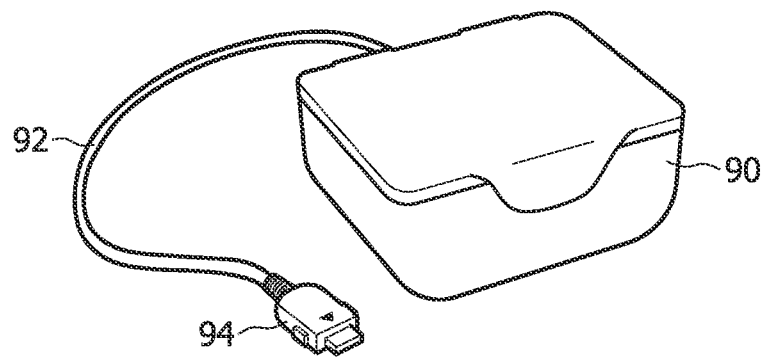
FIG. 9 illustrates a monitor charging dock and cord for recharging a cellphone handset.
Figure 10:
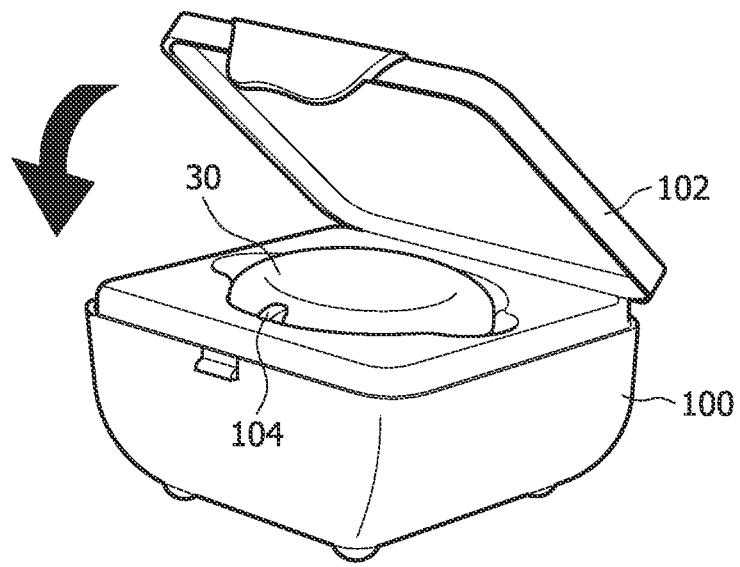
FIG. 10 illustrates a monitor inside the charging dock of FIG. 9 prior to closure of the lid of the charging dock.

A kit of the present invention also comes with a charging dock 90 as shown in FIG. 9 to recharge the ECG monitor 30 and the cellphone handset 50. FIG. 9 shows a charging dock of a constructed embodiment of the present invention, which includes a base unit 100 as shown in FIG. 10 with a hinged cover 102 for charging the monitor 30 and a cable 92 with a plug 94 for charging the handset 50. The a.c. power cord is not visible in these drawings. The monitor 30 is placed in its form-fitting space inside the base unit 100 as shown in FIG. 10 with its electrical contacts 36 facing downward. The space is keyed so that the monitor will only fit in the space when an LED 104 is positioned in the notch 34 of the monitor. With the lid 102 open as shown in the drawing, the monitor rests lightly on elastomeric charging contacts underneath the monitor. In other embodiments the contacts may be spring-loaded pins. The lid 102 must be closed for charging to begin; charging will not take place with the lid open. When the lid is closed the inside of the lid presses the monitor firmly against the charging contacts. This engagement is measured by the charging dock, which measures the impedance of the contact engagement. With the lid closed as indicated by the arrow in FIG. 10, the circuitry and software program inside the base unit 100 start to initialize and the LED begins to blink with an orange color. After initialization is complete, the charging circuitry begins to charge the lithium-ion battery inside the monitor 30 and the LED 104 emits a steady green light. As the monitor is being charged, the monitor begins wirelessly transmitting its archive of ECG data to the cellphone handset 50. The cellphone handset immediately relays the ECG data on to the monitoring center for analysis, reporting and storage. After successful receipt of the archive data has been acknowledged by the monitoring center, the ECG data in the monitor is erased or cleared from memory for receipt of new ECG data when the monitor is reattached to the patient.

Figure 11:
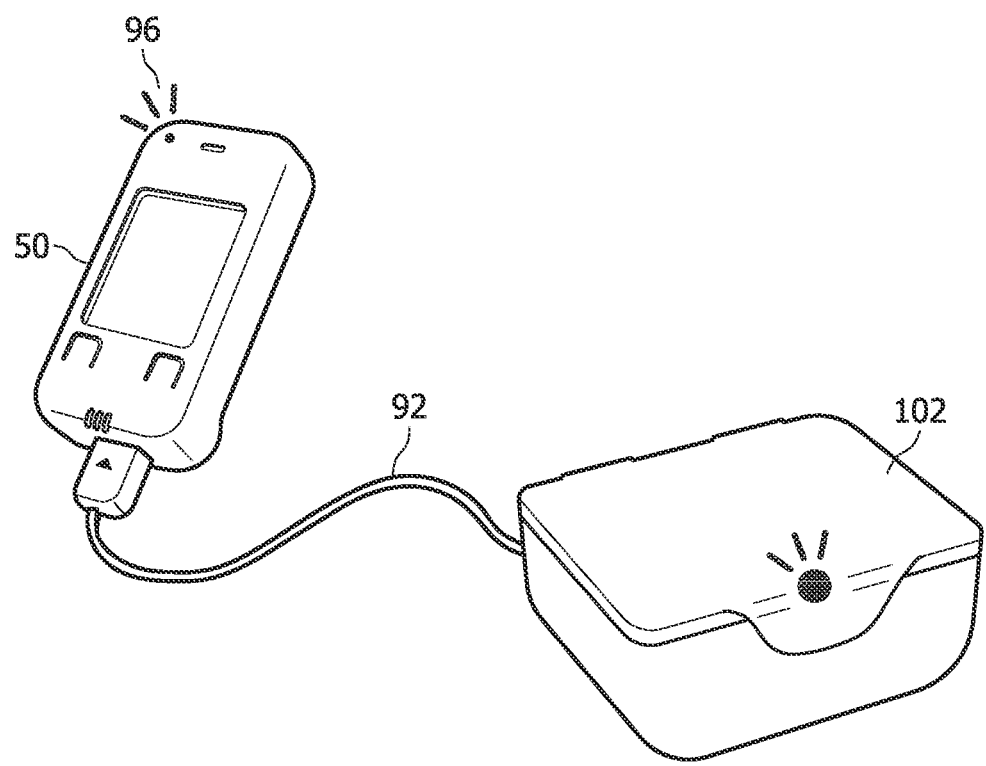
FIG. 11 illustrates a charging dock of an ECG monitoring system kit of the present invention while being used to recharge a monitor and a cellphone handset.

While the monitor 30 is being charged the cellphone handset 50 can be charged at the same time as shown in FIG. 11. The plug 94 of cable 92 is connected to the cellphone handset and the charging dock charges the cellphone handset at the same time as the monitor is being charged. In other embodiments the cellphone handset is recharged using a standard cellphone charger supplied by the cellphone manufacturer. As the cellphone handset is being charged a light 96 is illuminated on the handset to indicate that charging is taking place.

After the monitor 30 has been recharged and its archive data transferred to the cellphone handset from the charging dock, the circuitry and software of the monitor run a self-test of the monitor 30. Among the elements of the monitor which are tested are the random access memory of the monitor, reading and writing to the monitor flash card is tested, the motion channel of the monitor is tested, the wireless radio of the monitor is tested, and the analog and digital power supplies of the monitor are tested. A charging dock can also produce test signals which are applied to the electrode contacts of the monitor for testing the ECG circuitry of the monitor. If charging is not successful, the transmission of the archive data is not successful, or any of the self-tests is not successful, the illuminated LED begins to alternately flash orange and green to indicate that an error condition is present, and to inform the patient that a service call should be made to the monitoring center.

Figure 12A:
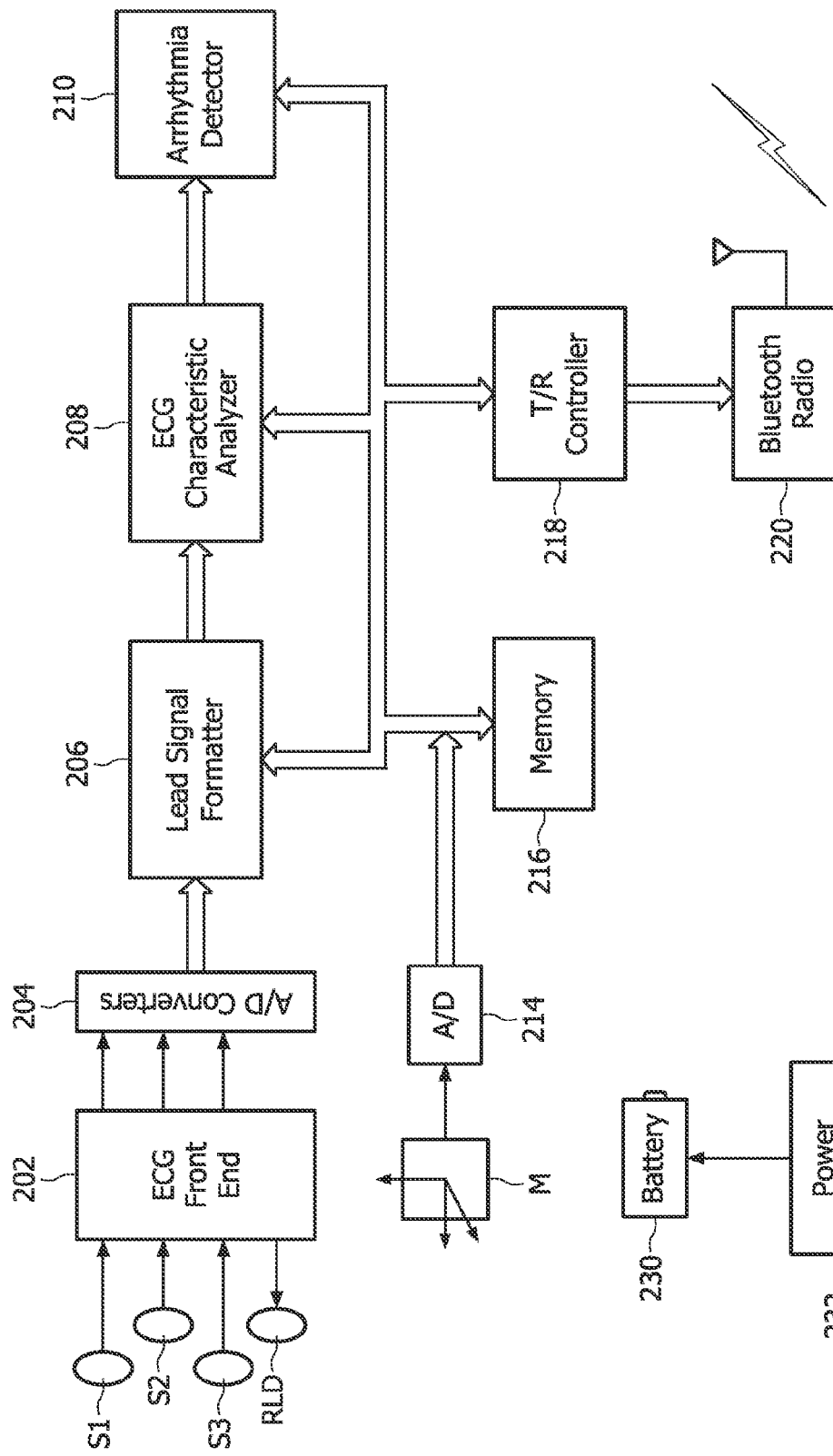
FIG. 12a is a functional block diagram of an ECG monitor constructed in accordance with the principles of the present invention.
Figure 12B:
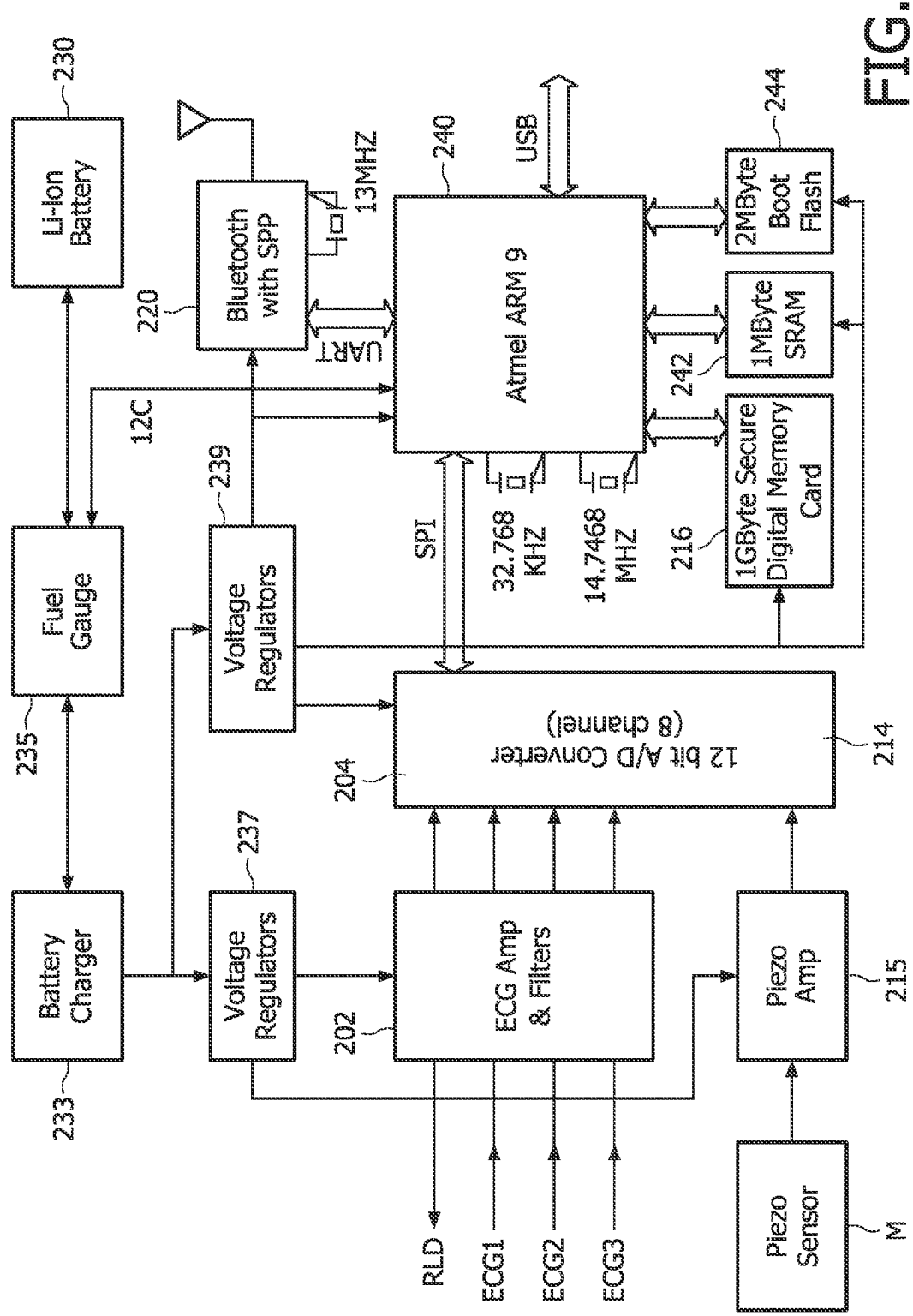
FIG. 12b is a block diagram of the function of the ECG monitor of FIG. 12a from a hardware perspective.

FIGS. 12a and 12b illustrate the functions and components of an ECG monitor constructed in accordance with the principles of the present invention, FIG. 12a from a functional perspective and FIG. 12b from a hardware perspective. The ECG electrodes s1, s2, s3 and RLD of the patch 20 are coupled to ECG front end circuitry 202. The ECG circuitry 202 amplifies and filters the ECG signals received from the body of the patient and injects a small signal to the RLD electrode to detect loose electrodes. Suitable ECG front end circuitry is described in international application number IB2007/054461 (Herleikson), filed Nov. 2, 2007, which is incorporated herein. A small 75 Hz signal is injected into the body from the RLD electrode and can be sensed at each of the s1, s2, and s3 electrodes. The signal received at each of the s1, s2, and s3 electrodes is applied to an input of a respective differential amplifier, along with a reference voltage formed by combining signals from the s1, s2, and s3 electrodes. If an electrode becomes loose on the body, the 75 Hz signal will be detectable at the output of the differential amplifier of that electrode. When the electrodes are properly in contact with the patient the signal will disappear as a common mode signal. A signal from the combination of the electrode signals is fed back to the RLD electrode as a feedback signal to balance common mode voltage and noise. The analog signals from the s1, s2, and s3 electrodes are converted to digital signals by A/D converters 204 by sampling at a 300 Hz rate. This sampling frequency is a multiple of the 75 Hz loose lead signal, enabling the 75 Hz signal to be easily filtered out. The digitized electrode signals are coupled to a lead signal formatter 206 which forms multi-vector lead signals s1-s2 and s1-s3. These two signals can be combined to compute a third vector, s2-s3. The three lead signals are formed in a manner equivalent to the manner in which the I, II, and III leads of a conventional ECG lead set are formed. The lead signals are coupled to an ECG characteristic analyzer 208 which defines characteristics of an ECG signal such as the QRS complex, the average beat, R-R interval and pulse rate. A suitable lead signal formatter and ECG characteristic analyzer are described in U.S. provisional patent application No. 60/954,367 (Zhou et al.), filed Aug. 7, 2007. The ECG characteristics are coupled to an arrhythmia detector 210 which analyzes the ECG for certain signal characteristics and threshold levels determined by the patient's physician and coupled to the arrhythmia detector, as described in detail below. If a sought-after arrhythmia is detected, that event is coupled to the transmit/receive controller 218, along with a 90-second ECG strip from 60 seconds prior to the occurrence of the event to 30 seconds after. The time of the event is marked in either the event information, the ECG strip, or both, and can be indicated as the time the event first appears in the ECG data, the time the event ends, the time the event was detected, or some other clinically significant time mark. The ECG strip and event information, which may be sent separately or merged together, are packetized and transmitted to the cellphone handset by a Bluetooth radio 220. This information and all of the ECG data received by the monitor are downsampled to a 200 Hz reporting rate and stored on a 2 GB flash card memory 216. A 2 GB memory can hold approximately 36 hours of ECG data at this reporting rate.

Located inside the monitor 30 is a motion detector M such as an accelerometer or a piezoelectric strip. The motion detector senses motion of the monitor while attached to the patient and hence motional activity of the patient. The motion signal from the detector is amplified, digitized by an A/D converter 214, and stored on the memory 216. The motion signal is a fourth data channel sent to the monitoring center along with the s1, s2, and RLD ECG signals and can be correlated with the ECG information to interpret possible patient conditions as described in international patent application publication no. WO2007/066270 (Solosko et al.) For instance, a pause in the ECG signal accompanied by a large motion signal could indicate that a patient with syncope has fainted.

The monitor also includes power management circuitry 232 which monitors the condition of the lithium-ion battery 230 and controls charging of the battery. A fuel gauge 235 monitors charge into and out of the battery and continually assesses the state of the battery, its charge level, and its capacity for recharging.

Since the monitor 30 is permanently sealed in this example with no external controls, there is no ability or need to turn the monitor on and off manually. As soon as the monitor is fully assembled in the factory, it begins operating immediately. However, if the monitor does not sense after a predetermined period of time that its contacts are engaged with contacts of a charging dock or a patch, the power management system of the monitor switches the monitor into a "sleep" mode. In the sleep mode the only circuitry kept operating is that which senses engagement with the contacts of a charging dock or patch, which consumes only a small amount of current. When the power management system senses this engagement, the monitor is turned on to its fully operational state. Thus, the monitor can remain idle in inventory for weeks or months and awake virtually fully charged when placed into service.

In a constructed embodiment the core of the monitor is a microcontroller 240 which receives the digitized ECG and motion signals and performs the lead signal formatting, analysis, and arrhythmia detection described above, as well as the transmission and receipt of data by the Bluetooth radio 220. The microcontroller also has a USB port which is coupled to the row of contacts on the back of the monitor case, enabling data and programs to be coupled to the microcontroller and its data storage devices 216 and 244.

Figure 13:
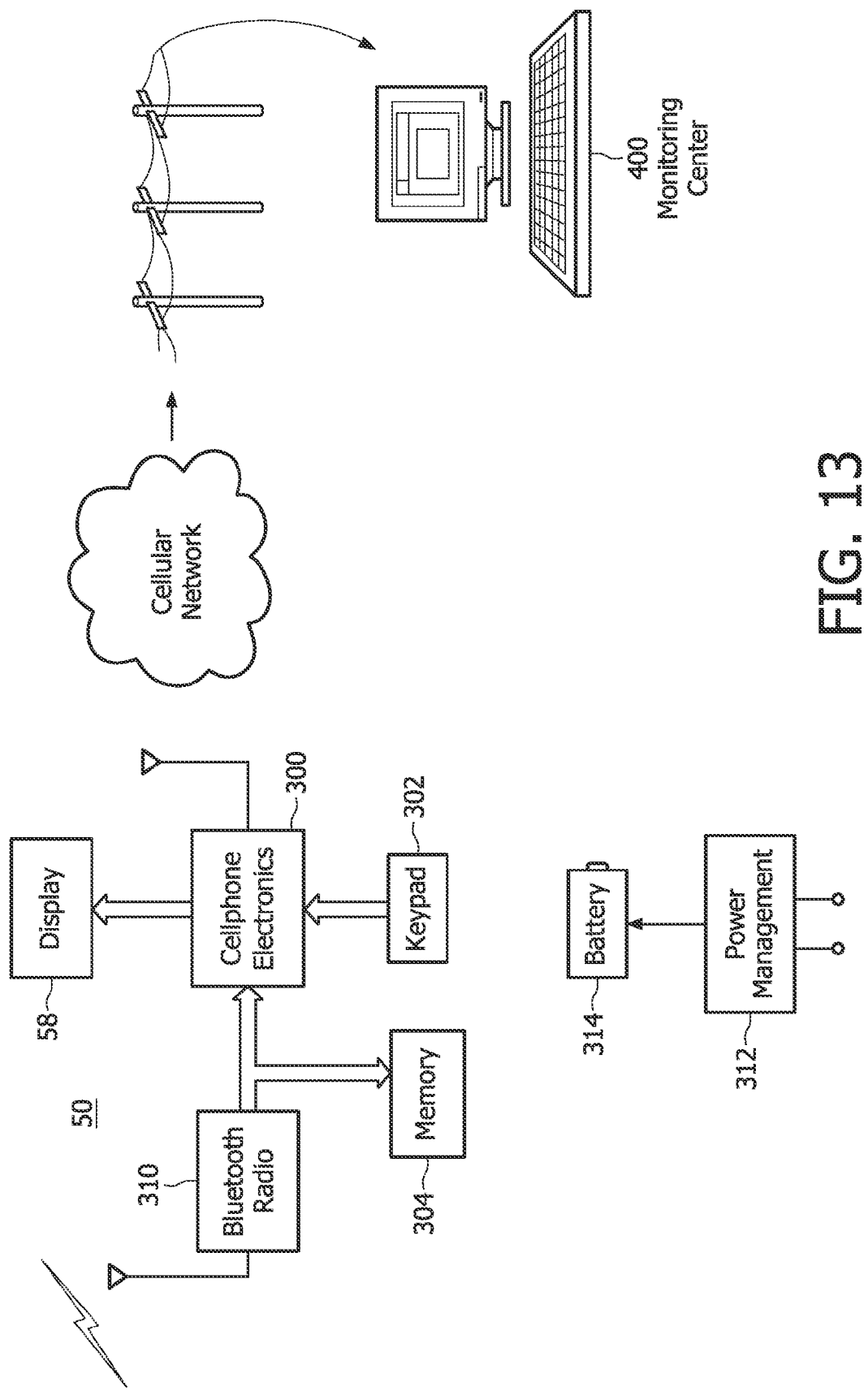
FIG. 13 is a functional block diagram of a cellphone handset in communication with a monitoring center.

FIG. 13 shows the balance of a monitoring system of the present invention, including a block diagram of the cellphone handset 50 and a communication link to a monitoring center 400. The cellphone handset 50 is a commercially available cellphone with a Windows Mobile operating system for a smart phone. The cellphone includes cellphone electronics which receives inputs from a keypad 302 and displays graphical information on a display 58. The cellphone handset 50 includes a Bluetooth radio 310 which communicates with one or more monitors 30. A 2 GB memory 304 stores programs and data such as ECG data transferred to the handset from an ECG monitor. The cellphone handset is powered by a battery 314 controlled and charged by power management circuitry 312. The Windows Mobile operating system enables the cellphone directory structure to be viewed by a personal computer when the cellphone is connected to the p.c. by the same (USB) cord 92 used to charge the battery 314. An executable program which controls the cellphone to operate as described herein is loaded into a memory of the cellphone, either memory 304 or the cellphone's built-in memory, along with graphics for the cellphone display as an installer routine. The startup directory of the operating system is modified with a link to the executable program so that, when the cellphone is turned on and boots up, it will automatically begin running the executable program and displaying the graphics designed for the monitoring application. The cellphone handset 50 communicates over a cellular network and then land lines to a monitoring center 400 which receives ECG data and status notifications from the ECG monitor and sends commands and configuration information to the monitor.

Figure 14:
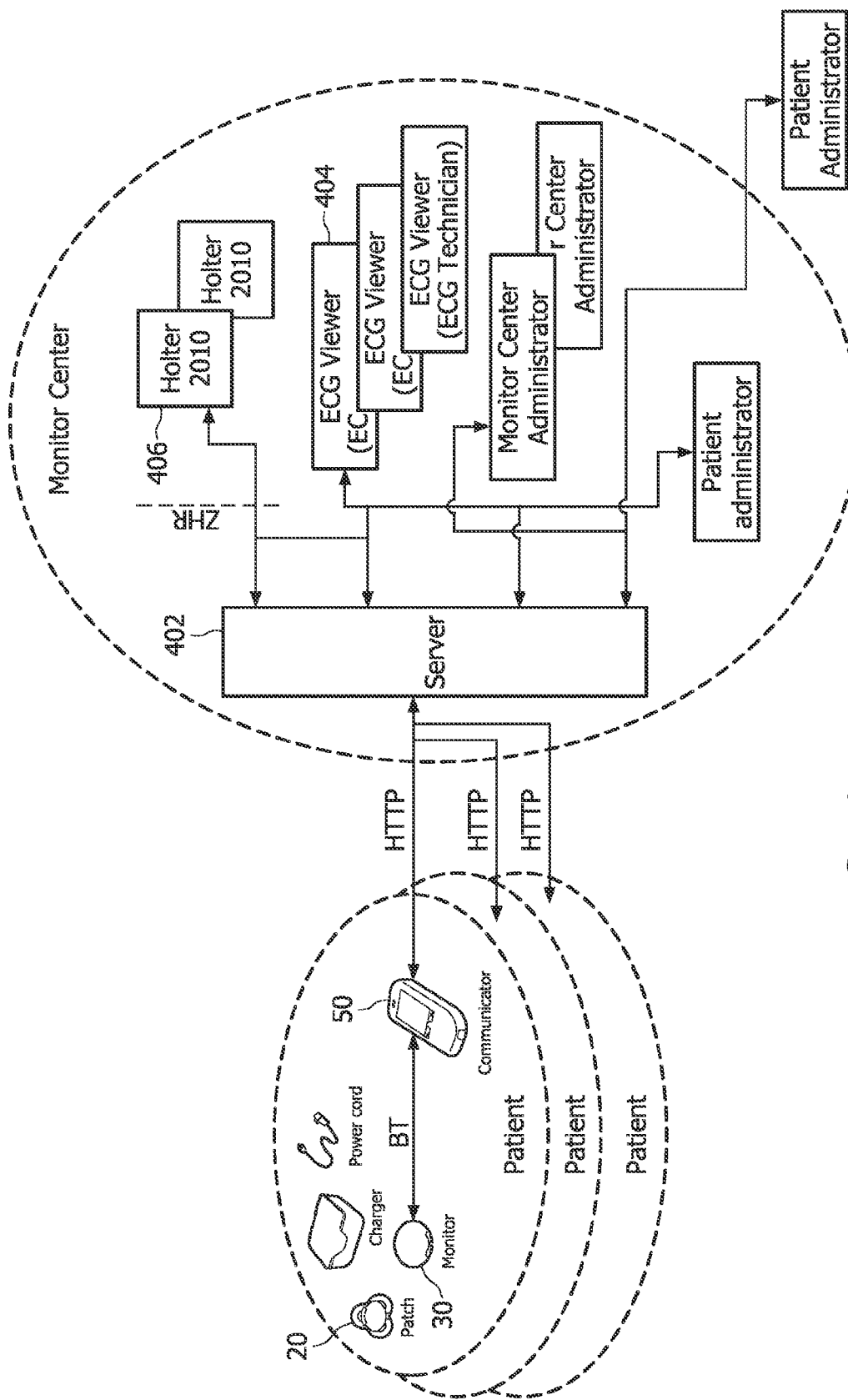
FIG. 14 is an illustration of the communication between an ECG monitor and a monitoring center and its functions for an ECG monitoring system of the present invention.

The interaction of monitoring components of the present invention which are with the patient and those that are at the monitoring center is shown in FIG. 14. The monitor communicates by Bluetooth (BT) with the cellphone handset 50. The ECG information is sent in an HTTP protocol to a server 402 at the monitoring center 400. If the transmission is at the time of an event, the accompanying ECG strip is viewed by an ECG technician on an ECG viewer 404. If the transmission is a daily archive of ECG data, it is sent to a Holter 2010 system 406 for triage and reporting. Reports from an event diagnosed by an ECG technician or daily reporting of an archive are forwarded to an onsite patient administrator or the administrator in charge of the patient and study. Overall coordination of the monitoring center is directed by one or more monitoring center administrators.

The transfer each day of a complete recording archive of full disclosure data, every heartbeat of the patient, enables subtle cardiac conditions to be diagnosed which may not be found with typical ECG strip reporting. For instance, a high heart rate alarm limit may be set to a level considerably above the patient's normal heart rhythm. Thus, a slight increase in the patient's heart rate may not be detected as a reportable event by the patient's arrhythmia detector. However, the slight increase in heart rate may recur numerous times in a short period of time, or may extend continuously over a long period of time. These more subtle behaviors of cardiac rhythm can be recognized by more sophisticated analysis systems operating on full disclosure data such as the Holter 2010 system mentioned above. The Holter 2010 system can be used to analyze each daily archive of data and produce a daily report which identifies such symptomatic patterns of heart rhythm. The identification of such subtleties in the daily archive by sophisticated analysis programs at the monitoring center can lead to a prompt diagnosis of the patient's condition or to the resetting of alarms and alarm limits to more effectively reveal characteristics of a cardiac condition.

A patient administrator such as the patient's physician may decide during a study to change the parameters of an arrhythmia which is to be detected. For example, the threshold for a detected tachycardia may be reset to 160 bpm. Such a change may be instituted by an ECG technician at the monitoring center, and the new setup sent to the patient's monitor as a configuration change. The new configuration information is dispatched by the server 402, received over the cellphone network by the cellphone handset, then forwarded over the Bluetooth link to the monitor 30, where it is installed in the arrhythmia detector.

FIG. 15 illustrates a setup screen which may be used to set up or reset thresholds for arrhythmia detection by the ECG monitor 30. In this example limits can be set from pulldown boxes for ventricular fibrillation, high heart rate, low heart rate, very low heart rate, asystole, pause in the heartbeat, and atrial fibrillation. In addition to detection limits, the user can also set a priority for an alert, such as urgent, medium, or low priority. When the ECG technician has set the desired thresholds and priorities, the configuration is saved with the "Save" button at the bottom of the screen. If the study has not yet started, the configuration information is stored on the server 402 at the monitoring center and uploaded to the monitor when the monitor is initially attached to the patient and its communication links are established. On the monitor's first communication with the monitoring center the monitor checks for configuration information, which is then uploaded and installed in the arrhythmia detector. If the study is already underway, the new configuration is immediately uploaded for installation on the monitor.

In addition to the seven standard arrhythmia alarms shown in FIG. 15, the user also has the opportunity to set a custom alarm for a particular patient. The box 160 at the bottom of the configuration screen of FIG. 16 contains a custom alarm which has been enabled for the illustrated configuration. The box 160 gives an example of some of the parameters which may be configured for a custom alarm setting.

Figure 17:
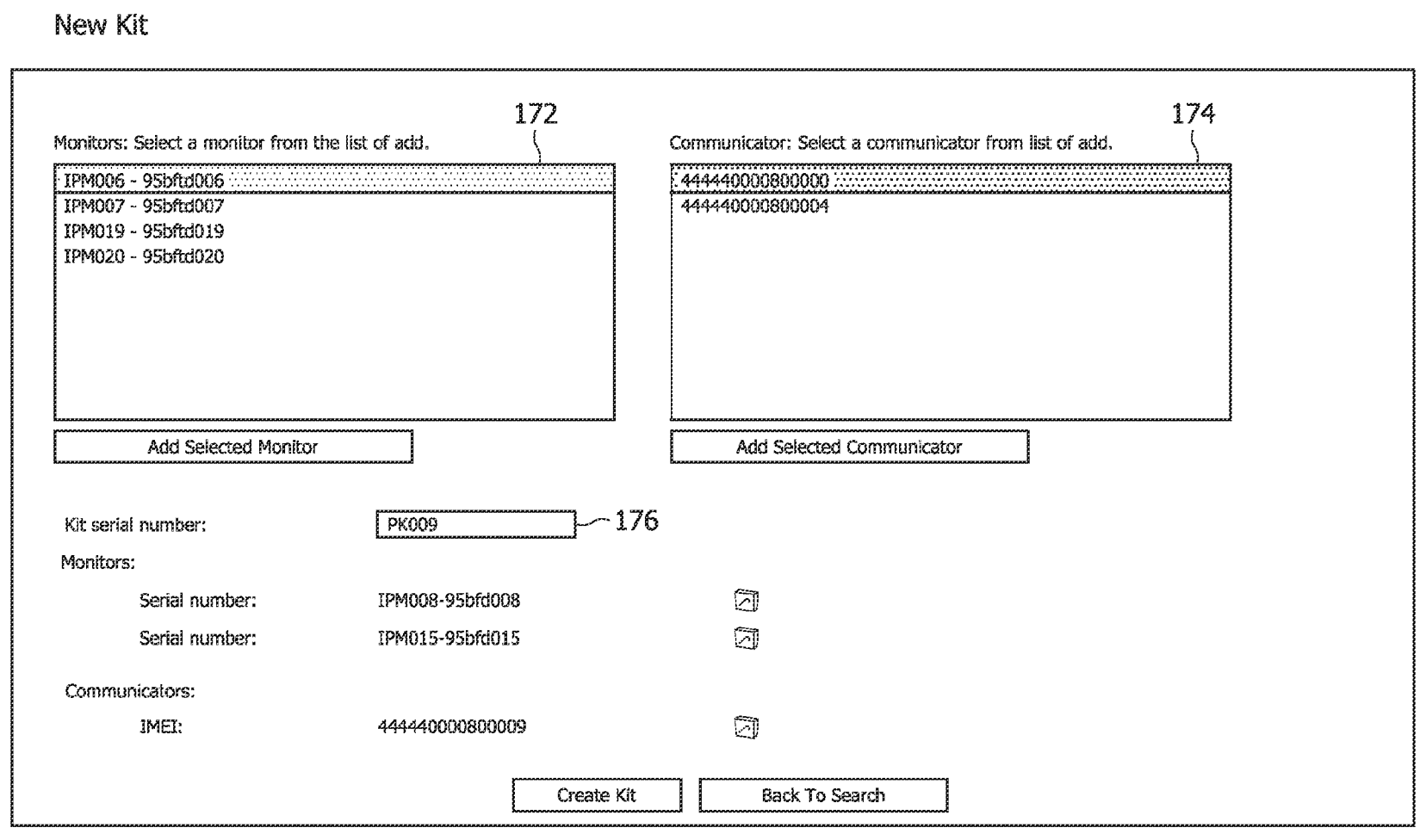

A monitoring system of the present invention is typically supplied as a kit of all of the components needed for a monitoring procedure. FIG. 17 illustrates a screen by which a monitoring or refurbishment center may assemble an ECG monitoring kit of the present invention from an inventory of ECG monitors 30 and cellphone handsets 50. A box 172 at the top of the screen displays a list of monitors 30 in inventory. An operator clicks on a monitor to highlight it, then clicks on the "Add Selected Monitor" button to add the selected monitor to the kit. Similarly, the operator can highlight a cellphone handset communicator in box 174 and click the "Add Selected Communicator" button to add a particular cellphone handset to the kit. The serial number of the kit being assembled appears in box 176 with the serial numbers of the monitors and cellphone handset shown below. When the operator is satisfied with the assembled kit, the "Create Kit" button at the bottom of the screen is clicked to assign the selected components to a particular monitoring kit.

FIG. 18 shows a screen by which an operator can track monitoring kits as they are sent to and received back from physicians, hospitals, and clinics. At the top of the screen are boxes by which an operator can search for a particular kit by entering the serial number for the kit in box 182, then clicking the "Search" button. Similarly the operator can pick another parameter against which to search for a particular kit. For instance, the operator can select a location to which a kit has been shipped in box 184, then search for all kits shipped to that location. The large box 186 at the bottom of the screen shows shipping information concerning a number of kits, including the date the kit was shipped to a user, the location of the user, and the serial numbers of the monitor and handset components of the kit. When a kit has been received by the refurbishment center as discussed below, the "Received Date" can be entered for the kit. The tabs at the top of the box 186 are used to mark particular kits as shipped or received.

FIG. 19 shows a screen by which an operator can track serial numbers and Bluetooth addresses for monitors and can pair a selected monitor with a Bluetooth address of a cellphone handset. Using the boxes at the top of the screen, the operator can enter a serial number to search for a particular monitor. The large box 196 at the bottom of the screen lists all of the monitors in inventory and their serial numbers and Bluetooth addresses. New monitors can be added to the inventory by entering their characteristic information in the small boxes at the bottom of the screen. FIG. 20 is a screen by which an operator can search for individual monitors by serial number, shipping dates, and by the locations to and from which they have been shipped. This screen also enables a search of monitors which have been received back from a user after a study is complete. The large box 250 at the bottom of the screen lists the search results of monitors by their kit serial numbers, dates they were shipped to a location, and the dates the monitors were received back from those locations.

FIG. 21 shows a screen by which an operator can search for cellphone handsets by serial number, Bluetooth address, or phone number. The large box 252 at the bottom of the screen lists the search results for cellphone handsets and their identifying numbers, and enables new handsets to be added from the small boxes at the bottom of the screen.

The screen of FIG. 22 is similar to the monitor screen of FIG. 20 and allows cellphone handsets to be searched and listed by shipping location and kit serial number. This screen also enables tracking of cellphone handsets as they are returned from a user.

Figure 23:
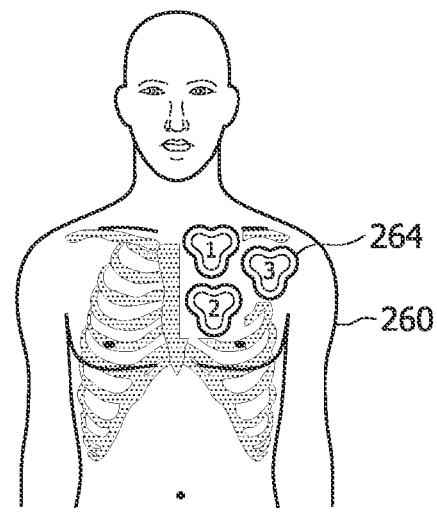
FIG. 23 illustrates a computerized template used to record suitable electrode patch placement locations and patch orientations for a patient.

When a physician or nurse is outfitting a patient with a monitoring kit for a study, one of the first tasks is to find locations on the patient's chest where the patch can be applied so that the attached monitor will receive a strong ECG signal. Furthermore, it is desirable to find a number of acceptable locations so that one location on the chest is not used repeatedly, potentially causing skin irritation from repeated use. FIG. 23 shows an interactive screen by which the nurse or physician can record information concerning patch placement. At the top of the screen is data concerning the procedure or study, such as start date and end date of the procedure. The screen can also record the dates on which the patch positions were updated and who updated the information. The body template of figurine 260 at the bottom of the screen shows three patches over the left side of the chest. These patch graphics can be dragged to different positions on the torso template, rotated if required, and then dropped to record an acceptable chest location for attachment. A suitable location on the patient's chest may be found by clipping a monitor into a patch and peeling away the portion of the release liner of the patch which covers the electrode locations, as described in U.S. provisional patent application No. 60/869,009 (Cross et al.), filed Dec. 7, 2006. The patch can then be placed and repositioned to multiple chest locations with the hydrogel of the electrodes conducting ECG signals to the monitor. Alternatively as described in the Cross et al. patent application, if the release liner has conductive coverings over the electrode locations, the patch and monitor can be maneuvered to find suitable locations without peeling away the release liner. Each time a suitable location is found, a patch graphic 264 is repositioned over the body template 260 to mark the identified location. The screen of FIG. 23 can be saved and referred to each time a new patch is to be applied by the nurse or physician during the study, or a printed copy taken home by the patient and referred to each time it is necessary to replace a patch. Alternatively or additionally an electronic copy of the body template can be displayed on the cellphone handset display 58 to guide the patient when replacing a patch. Patches can normally be worn for about three days before they need to be replaced.

FIG. 24 shows a screen which is used to record information about a procedure including the time each day when a patient is to be reminded to recharge the monitor and the cellphone handset. This screen is normally filled in when the monitoring kit is first given to the patient and the patient decides when he or she is going to recharge the monitor and handset. In a typical procedure the patient will wear the monitor and the handset all day as the patient goes about his or her normal daily activities. At the end of the day when the patient retires for the night is a convenient time to recharge the monitor and the cellphone. The patient will take a recharged monitor from the charging dock 90, remove the monitor in use from the patch and place it in the charging dock, and snap the freshly charged monitor into the patch. Just before getting into bed the patient will attach the cellphone handset to the cord 92 of the charging dock. The used monitor and the cellphone can then recharge during the night. The cellphone is left on at all times, and the charging dock is preferably left on a bedside table so that the charging cellphone handset will remain in range for Bluetooth communication with the monitor on the patch as the patient sleeps. While the patient sleeps the used monitor is recharged, its archive data sent to the cellphone and on to the monitoring center, the monitor self-tests performed, and the previous day's archive data cleared from memory in preparation for the next daily use of the monitor. It is preferable for the kit to include two monitors so that one can be worn for monitoring while the other is being recharged and its archive data transmitted to the monitoring center. Typically, the patient will retire for the night wearing the freshly charged monitor while the used monitor is in the charging dock being recharged during the night and transmitting its archive of ECG data to the cellphone handset and on to the monitoring center. If the patient experiences a detected arrhythmia during the night, the event notification and ECG strip are sent to the cellphone handset by the Bluetooth link and immediately sent on to the monitoring center by the handset. Both monitors, the one being worn by the patient and the one in the charging dock, are in Bluetooth communication with the cellphone handset at this time and events detected by the monitor being worn by the patient are immediately sent to the monitoring center without waiting for completion of the archive data transfer, either on a priority interrupt or time-interleaved basis.

If the patient forgets to place the monitor in the charging dock so that its archive data can be uploaded to the monitoring center or is otherwise unable to do so, the patient will be prompted by the cellphone handset to do so, as shown in FIG. 8d. If the patient dismisses the prompt or ignores the prompt and continues to wear the monitor, there may come a time when the memory of the monitor has been completely filled with recorded ECG data. In this situation the monitor will begin to operate as a loop recorder. Newly acquired ECG signal data will be stored in the memory and the oldest stored ECG data in the memory will be overwritten and lost.

When the patient gives the physician or nurse a schedule of the time each day when the patient expects to start the recharging procedure, the time for each day is recorded on the screen of FIG. 24. A printed copy of the screen may then be given to the patient to take home. In addition, the screen is forwarded to the monitoring center and the charging reminder times sent as configuration information to the patient's monitor or handset. At the appointed time each day, a recharge reminder message will appear on the screen 58 of the handset (see FIG. 8d), accompanied by a tone or voice prompt to draw the attention of the patient to the reminder. The schedule can be easily changed by sending different reminder configuration information to the monitor or handset.

FIG. 25 shows a screen by which the reporting requirements of the physician can be recorded by the monitoring center. This screen shows the procedure start and end dates at the top of the screen. On the "Reports deliver" section of the screen are listed the time when a daily report will be sent to the physician and the mode by which it will be sent. Generally, the physician will receive a report each day of the previous day's events and an analysis of the previous day's 24 hours of ECG information from the daily ECG archive of data. This example also shows the time and date when the reports delivery section was updated.

Reports and patient information may be posted on the server 402 at the monitoring center for access by particular accounts. An account may be an individual physician, hospital, or clinic. Patient information must be password-protected for the security of individual patient data. FIG. 26 illustrates a screen by which the monitoring center may track activity of a particular account. The top of the screen gives status information and information about the account's password and its use. A high number of failed attempts to gain password access may be an indicator of someone seeking unauthorized access to the account information, which needs to be investigated. Login activity for the account is also tracked on this screen. The list in box 262 at the bottom of the screen shows individual sessions when the account logged onto and out of the server including the time of the session.

FIG. 27 is a screen showing a patient communication log with the monitoring center. The search boxes at the top enable an operator to search for patient information by site, physician, or patient. The search results, showing patients, their physicians, their procedures, and the procedure dates are returned in box 272. Detail for a selected patient is shown in box 274. The most recent communication between the patient and the monitoring center is recorded at the top of the box, and earlier communications are listed at the bottom of the box.

Figure 28:
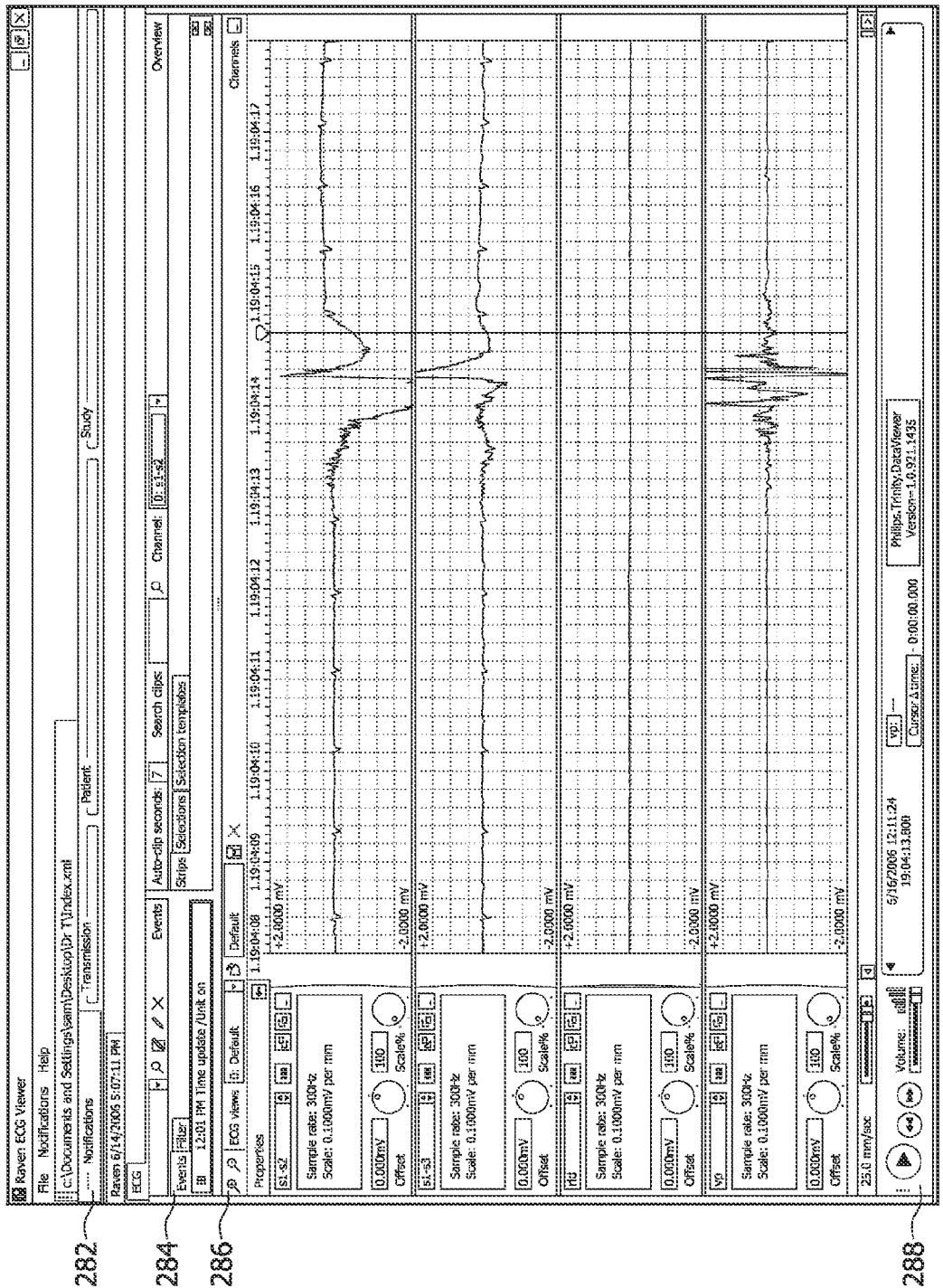
FIG. 28 illustrates a screen display of an ECG viewer used to display the data produced by a four channel ECG monitor constructed in accordance with the principles of the present invention.

FIG. 28 illustrates an ECG viewer screen suitable for receiving and analyzing event information received at the monitoring center from an ECG monitor of the present invention. In this embodiment the ECG viewer screen has three major sections: a Notification window 282 which shows information about a particular procedure or study and lists the notifications received from that patient; an Events window 284 which displays the information received at the time of an event; and an ECG viewing window 286 in which the data received over the channels transmitted by the monitor may be analyzed in detail. In FIG. 28 the Notification and Events windows are unexpanded and the ECG viewing window is expanded. In this embodiment the ECG monitor 30 transmits five channels of data and the cellphone handset transmits a voice channel recorded with the handset. The data channels are three ECG signals, s1, s2, and s3 in this example, the RLD signal ("rld"), and the motion channel ("vp"). Differential lead signals s1-s2, s2-s3, and s1-s3 may be derived from the ECG signals of this example. The RLD signal may be used to further process and refine the lead signals and identify noise conditions. The controls at the left of each display strip allow an operator to adjust the scaling and other parameters of the strip display. In the display strips of this example it is seen that a significant motion signal has occurred at the time of the sizeable ECG signals of the s1-s2 and s1-s3 channels. The audio controls 288 at the bottom of the display enable a transmitted voice recording from a patient to be replayed by the ECG viewer operator.

Figure 29:
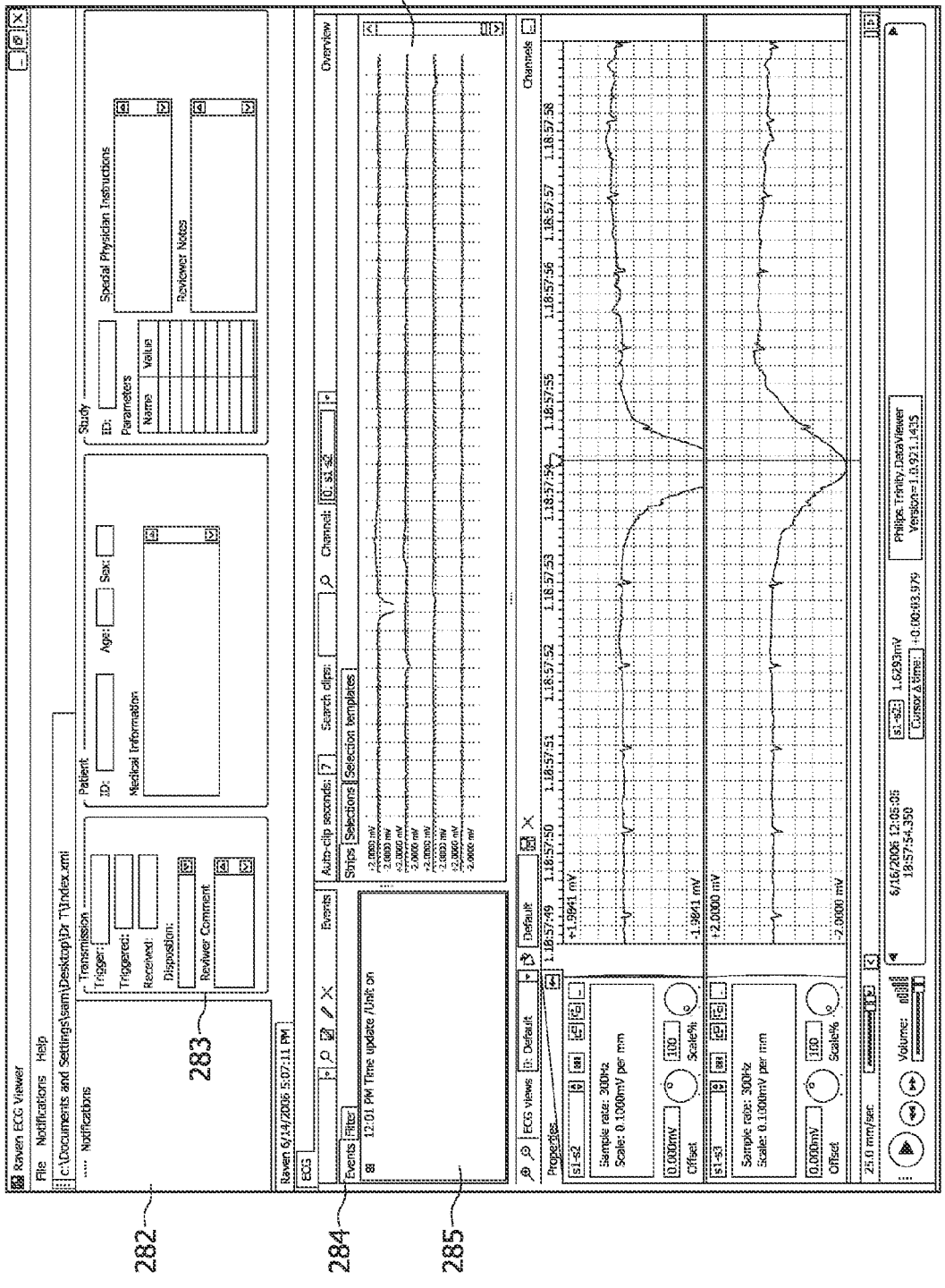
FIG. 29 illustrates a screen display of an ECG viewer for an ECG monitor of the present invention with the notification and event windows expanded.

FIG. 29 illustrates the ECG viewer screen of FIG. 28 with the Notification window 282 and the Events window 284 expanded. In a constructed embodiment the monitor 30 sends a notification every time the status of the monitor changes and these notifications, as well as those originating from status changes of the cellphone handset, are forwarded on to the monitoring center by the cellphone handset. For example, when the monitor senses that it is attached to a patient and receiving ECG signals from the patient, a status message is sent to the monitoring center. When the monitor detects a loose lead, a status message is sent to the monitoring center. When the loose lead is reattached a status message is sent to the monitoring center. When the monitor is removed from the patch a status message is sent to the monitoring center. Thus, the continual flow of status messages enables the monitoring center to evaluate the patient's use of the monitor and the technician at the monitoring center can intervene with a call to the patient's cellphone handset if the flow of messages indicates that the patient is having a problem or overlooking something. Table 1 below lists some of the typical messages which may be sent during use of a monitoring system.

TABLE 1

| Notification | Type |
| --- | --- |
| Monitor on patient, operating properly | Status |
| Loose lead | Status |
| Loose lead corrected | Status |
| Monitor removed from patient | Status |
| Monitor powered down | Status |
| Low battery (monitor) | Status |
| Low battery (handset) | Status |
| ECG streaming mode | Status |
| Bluetooth communication lost | Status |
| Bluetooth communication restored | Status |
| Cellphone communication lost | Status |
| Cellphone communication restored | Status |
| Self-test successful | Status |
| Self-test unsuccessful | Alert |
| Monitor placed in charging dock | Status |
| Monitor removed from charging dock | Status |
| Monitor charging started | Status |
| Monitor charging completed | Status |
| Monitor charging unsuccessful | Alert |

TABLE 1-continued

| Notification | Type |
|---|---|
| Cellphone charging started | Status |
| Cellphone charging completed | Status |
| Cellphone charging unsuccessful | Alert |
| Charging dock error | Alert |
| ECG archive transmission start | Status |
| ECG archive transmission complete | Status |
| Event information + ECG strip transmitted | Alert: priority = hi, med, low |
| Voice message + ECG strip transmitted | Alert: priority = hi, med, low |

Different notifications can be handled in different ways. For example, interruption of Bluetooth communication may be a common occurrence. A patient may set the cellphone handset down and walk away to perform some task, resulting in a loss of Bluetooth communication when the monitor is out of range with the cellphone handset. A few minutes later the patient returns to the cellphone handset and picks it up and puts it back in the carrying case, a purse or pocket, which re-establishes the Bluetooth communication when the monitor and cellphone handset are back within Bluetooth signal range of each other. In such circumstances it may be desirable to delay notification of Bluetooth communication loss for five or ten minutes to allow a period of time for communication to be restored before sending a notification. Alternately, the communication loss notification may be sent immediately as a status message, and if a notification that communication has been restored is received shortly thereafter, the notification canceled or automatically marked as resolved. If the resolution notification is not received within five or ten minutes or some other predetermined period of time, the priority of the notification is raised at the monitoring center to bring it to the attention of a technician. Loose lead notifications may similarly be delayed or subject to priority escalation to allow the patient to recognize and correct the situation without a notification being sent or responded to by the monitoring center.

It will be appreciated that different status notifications can originate from different sources. A notification that Bluetooth communication has been lost must originate from the cellphone handset since the monitor is out of communication with the handset at this time and cannot originate the message. Similarly a notification that cellphone communication has been lost will originate at the monitoring center, generally when the monitoring center tries to send a message to the cellphone and finds that it is unable to do so.

In the example of FIG. 29 all notifications received from the patient are listed in the Notifications box 282. Routine status notifications appear in normal text and in chronological order of receipt. Higher priority alerts are displayed at the top of the list of notifications and are color-coded to indicate urgency, for example, yellow highlighting for medium priority alerts and red highlighting for high priority alerts. In a preferred embodiment, ventricular fibrillation and asystole events are of the highest priority, heartbeat pauses and heart rate notifications are next in priority, loose lead and poor electrode contact notifications are lower in priority, and other status changes and technical alerts such as low battery and loss of communication are of the lowest priority. As the notifications are reviewed by an ECG technician at the monitoring center they may be processed appropriately then deleted from the displayed list. The second box 283 in the Notification window 282 has entry spaces where the technician can enter a disposition for the notification and provide appropriate comments with the disposition. The Notification window thereby provides a task list which the technician can use to review and handle notifications from a patient's monitor in a priority order and efficient manner. In a constructed embodiment multiple technicians may view the notifications from the same patient at the same time, but when a technician has selected a particular notification to analyze and disposition, the other ECG viewers are locked out from selection of the notification so that only one technician can work on disposition of a notification at any given time. This prevents redundant processing of a single notification and enables flexibility in the operation of multiple ECG viewers at a large monitoring center.

The status notifications can also be displayed on a separate screen as shown by the screen display of FIG. 30. As this example illustrates, low priority mode change status notifications are listed below the higher priority event "alarm HRLo" at the top of the list. Notifications which have been dispositioned by a technician are marked by a check mark in the box at the left side of a notification. The boxes at the top of the screen are used to search for notifications of certain characteristics, such as Event notifications or notifications received during a selected time period.

When an Event notification is received, including a patient voice recording, the Event notification is accompanied by a 90-second ECG strip which was recorded starting sixty seconds prior to the event time and continuing for thirty seconds thereafter. Event notifications will appear in the Event window 284. The identity of the event is displayed in the first box 285 and the ECG strip transmitted with the event notification appears in box 287. The ECG technician can thereby quickly review the ECG signal from the time of the event. If more detailed analysis is desired, the ECG strip can be reviewed in the larger ECG viewing window at the bottom of the viewer screen as shown in FIG. 29.

Figure 31:
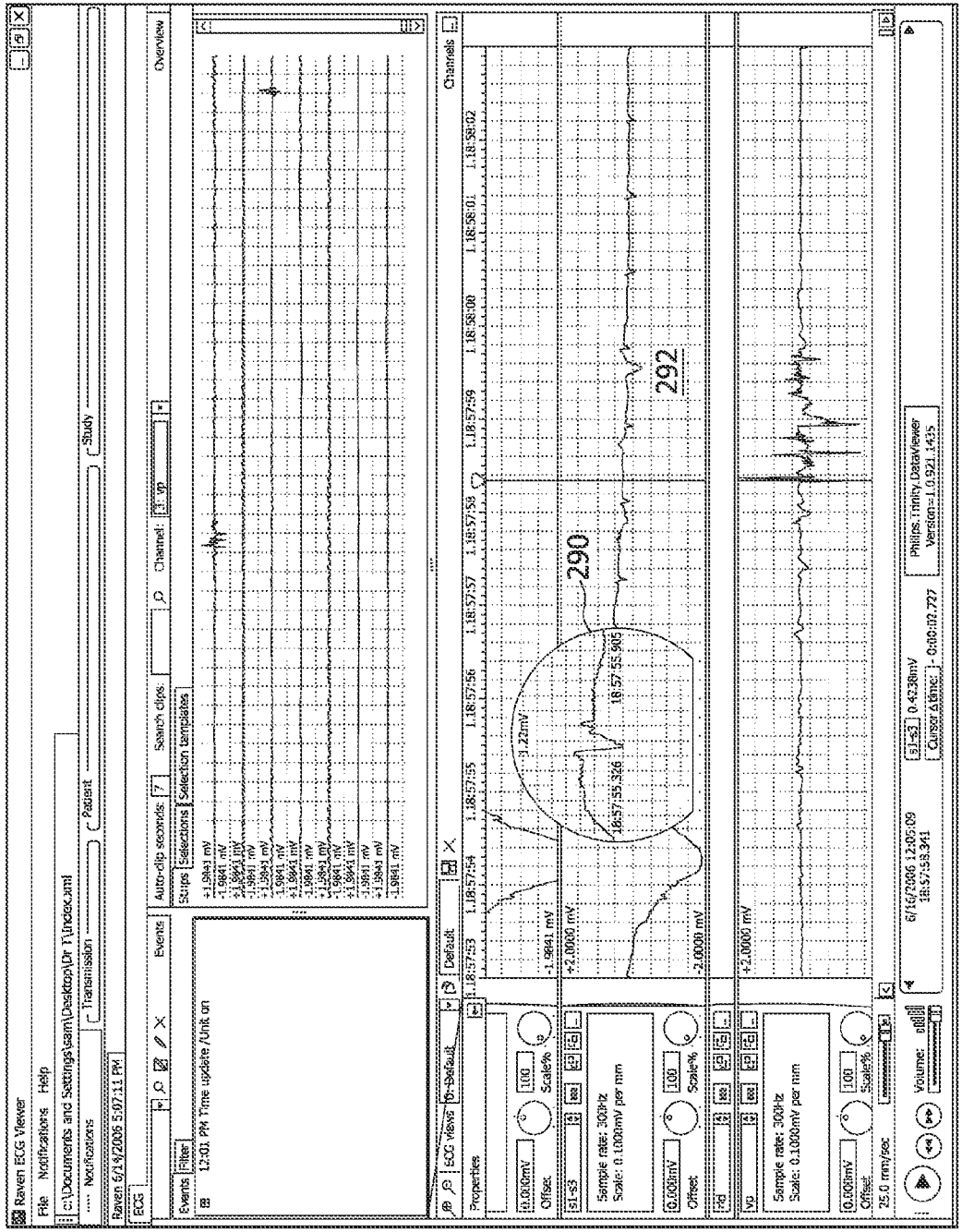
FIG. 31 illustrates a screen display of an ECG viewer with a magnification window for detailed examination of an ECG waveform in accordance with the principles of the present invention.

FIG. 31 illustrates a feature of a constructed embodiment of the present invention, which is an ECG magnifier window 290. The ECG technician can right-click on an ECG strip window 292 when it is desired to view an ECG waveform in greater detail. A list of option will appear and the technician selects "magnifier", causing the circular magnifier window 290 to appear. A central area of the ECG strip where the magnifier window 290 is located is then shown in an enlarged view in the window 290. A setup option allows the user to determine the degree of magnification (e.g., 2×, 5×, 10×) to be provided within the magnifier window 290. The user can drag the magnifier window across the ECG strip window 292 to enlarge any section of the displayed ECG strip.

Figure 32:
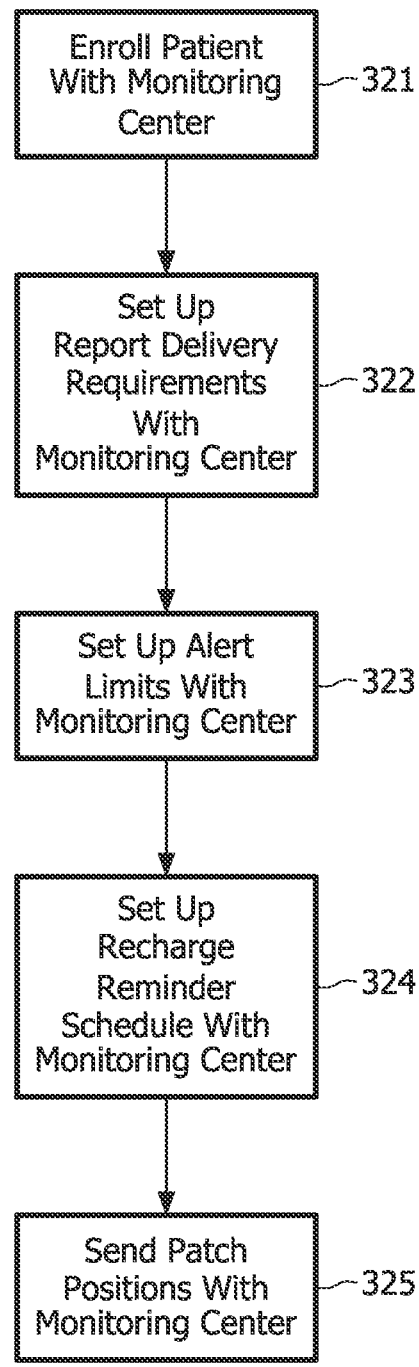
FIG. 32 is a flow diagram of a method for setting up an ECG monitoring procedure in accordance with the present invention.

FIGS. 32-37 illustrate steps by which certain activities attendant to the use of an ECG monitoring system of the present invention may be conducted. FIG. 32 is a sequence of steps performed when a patient is registered for an ECG monitoring procedure. At 321 the patient's physician enrolls the patient with a monitoring center. Patient information is given to the monitoring center and the monitoring center begins to prepare to receive notifications from the kit to be used by the patient. The physician may already have a kit on hand which can be used by the patient. If not, the monitoring center dispatches a kit to the physician for use by the patient. The monitoring center associates the kit to be used by the patient with the patient being enrolled by the physician. At 322 the monitoring center sets up the reporting requirements desired by the physician using a screen such as that shown in FIG. 25. At 323 the types of arrhythmia alerts to be monitored are set up using a screen such as those shown in FIGS. 15 and 16, and alarm limits are set as illustrated on those screens. At 324 the monitoring center sets up the reminder schedule for the times at which the patient will be reminded to recharge the handset and monitor as illustrated in FIG. 24. If the physician has completed a patch position chart such as that illustrated in FIG. 23, the chart is sent at 325 to the monitoring center for use by monitoring center technicians in assisting the patient with patch application if necessary. In other instances the patch position chart may be sent to the monitoring center at a later time. It will be appreciated that most or all of the information provided in the steps of FIG. 32 may be provided by the physician completing the enrollment and setup screens remotely in the physician's office without person-to-person contact with the monitoring center. That is, the setup screens can be made available to an account of the monitoring center as a Web accessible application. Once the information has been entered at a remote terminal it is available at the monitoring center, which can process and enroll the patient without personal contact with the physician.

Figure 33:
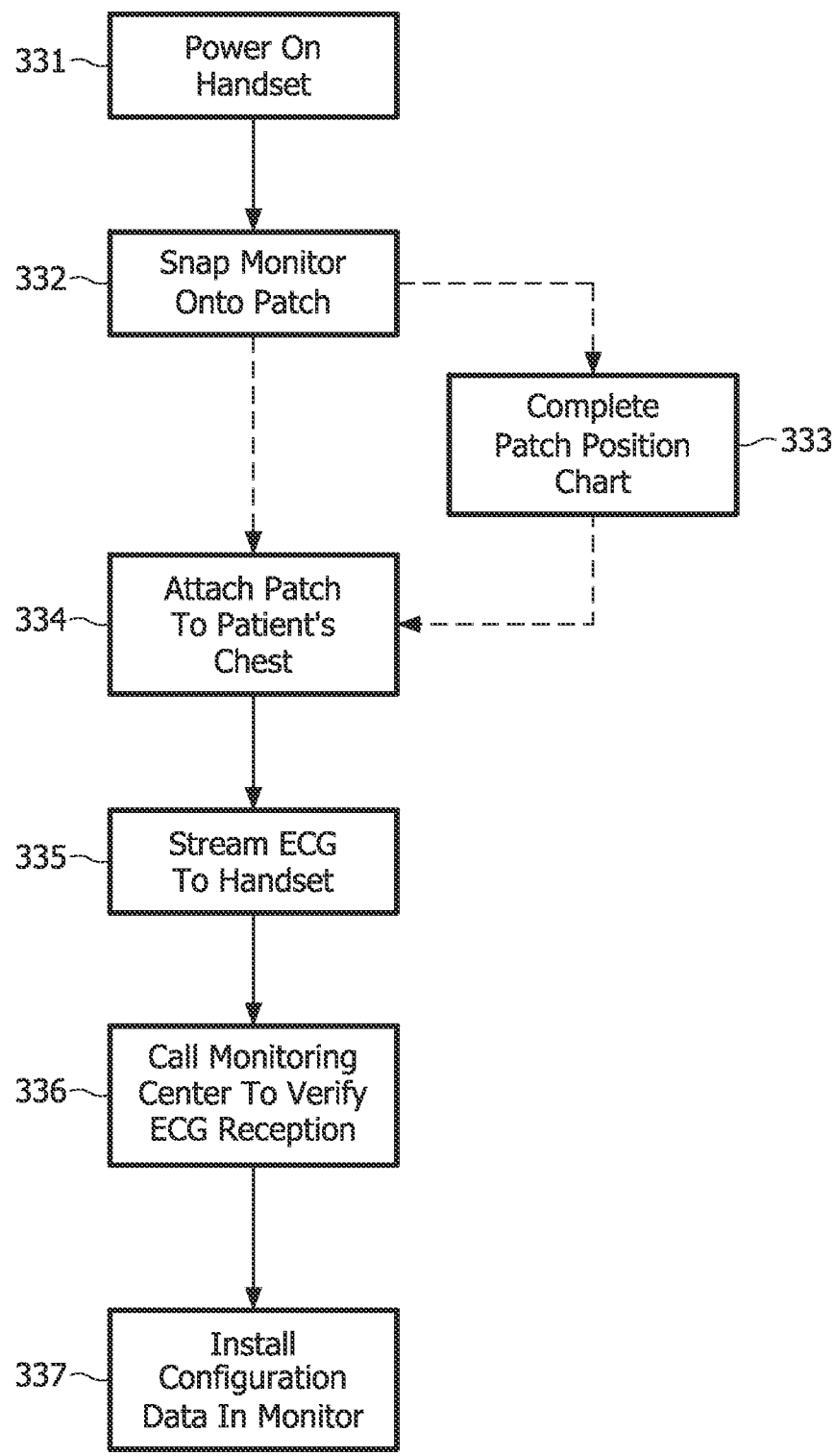
FIG. 33 is a flow diagram of a method for initially outfitting a patient with an ECG monitor in accordance with the present invention.

FIG. 33 illustrates a sequence of steps performed when the patient is initially introduced to a monitoring system of the present invention. At 331 a physician or nurse turns on the cellphone handset 50 and keys the handset to the ECG streaming mode. The monitor 30 is snapped into a patch 20 at 332 and the perforated center of the release liner is removed from the patch to uncover the gel electrodes. If locations for patch attachment have not previously been located on the chest of the patient, the clinician slides and/or rotates the patch and monitor over the patient's chest as described above to locate one or more suitable locations and orientations for patch attachment at which a clear ECG signal is be received, as indicated by the streaming ECG display. As suitable chest locations are found the patch position chart is filled in at 333 to record the locations, the chart is sent to the monitoring center and a copy given to the patient, step 325 of FIG. 32. The release liner is fully removed from the patch 20 to expose the adhesive and the patch and monitor attached to one of the ascertained locations on the patient's chest at 334. Channels of the ECG data should now stream to and appear on the handset display 58, verifying operation of the Bluetooth communication link between the monitor 30 and the cellphone handset 50 at 335. The clinician can reset the cellphone handset to normal operation by depressing the left "Exit" button shown in FIG. 8b and call the monitoring center at 336 to verify the second connection link, that between the cellphone handset and the monitoring center. Alternatively the control software of the cellphone handset can be programmed to make this connection automatically. A technician at the monitoring center can verify the complete communication path by, for instance, sending a command to the monitor to transmit an ECG strip to the monitoring center and verifying its receipt on an ECG viewer at the monitoring center. Communication with the monitoring center may indicate the need to further reposition the monitor and patch. When the cellphone handset 50 relays the first message from the monitor 30 to the monitoring center, the monitoring center responds by transmitting the configuration data for the procedure to the monitor 30. The configuration data and its arrhythmia alert limits are installed in the monitor at 337 and the monitor is then ready to proceed with the study.

Figure 34:
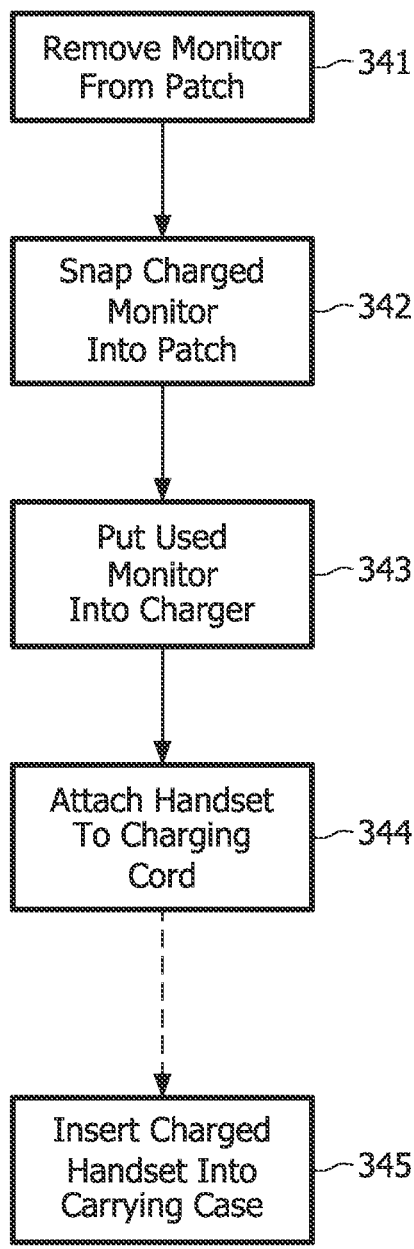
FIG. 34 is a flow diagram of a method for daily replacement and charging of an ECG monitor in accordance with the present invention.

When it is time to exchange monitors and recharge the used monitor, the sequence of steps shown in FIG. 34 can be followed. At 341 the patient removes the monitor 30 from the patch 20. If the patch needs to be replaced, the patch 20 is removed from the chest and a new patch attached to a new area of the skin to avoid irritation, using the patch position chart of FIG. 23. The monitor which was recharged the previous day and is still in the charging dock 90 is removed from the dock and snapped into the patch at 342. The used monitor is placed into the charging dock and the lid 102 closed at 343, and the cellphone handset is attached to the charging cord 92 at 344. Preferably this procedure is carried out at bedtime with the charging dock located next to the patient's bed so that the patient can go to bed and remain within Bluetooth communication range of the charging handset 50. When the patient gets out of bed in the morning, the charged handset is removed from its charging cord and put into the carrying case on the patient's waist at 345.

It will be appreciated that the wireless communication links of the system, the Bluetooth link between the monitor 30 and the handset 50, and the link between the cellphone handset and a cell tower, can be disrupted due to a variety of causes. Bluetooth communication range is usually a matter of feet, and it is generally recommended that the patient keep the cellphone handset within six feet of the patient to maintain this communication. If a patient puts the cellphone handset down and walks away for a period of time, this line of communication will be broken. Likewise, a patient with monitor and handset can travel out of range of a cellphone transceiver and cellphone communication will be lost. As another example, if a patient is going to travel by airplane, aviation regulations require that the cellphone handset be turned off before the plane departs and kept off until the plane lands. Thus, cellphone communication can be intentionally unavailable for a period of many hours.

Disruption of the Bluetooth link does not disrupt operation of the monitor 30. The monitor will continue to receive ECG signals from the patient and continue to analyze the heart information and store the data in the memory 216 of the monitor, even if the Bluetooth link is not operating. If an arrhythmia event is detected it will not be possible to transmit the event data or other status message to the cellphone handset 50 until the Bluetooth link is restored, however. Generally an out-of-range timeout will be allowed to expire before a loss of Bluetooth communication status message is sent to the monitoring center by the cellphone handset to allow the activity of the patient to restore the link before reporting the status change. When the Bluetooth link is restored the event data and its ECG strip and all other pending notifications are immediately sent to the cellphone handset for relay on to the monitoring center. Preferably the Bluetooth radio is operated in the "sniff" mode, a low power mode in which synchronization between a Bluetooth transmitter and receiver can be maintained for short intervals and quickly re-established. When the monitor has a message to send, the Bluetooth transmitter is returned to full power for transmission of the message. The Bluetooth link is operated in full duplex so that either the monitor or the cellphone handset can initiate transmission of data to the other component. The monitor will continue to "sniff" for the cellphone handset while communication is disrupted so that, when the handset is back in range, pending messages such as event and status data can be sent to the handset and monitoring center immediately at that time.

If the Bluetooth link is operational but cellphone service is disrupted, communication will continue between the monitor 30 and the cellphone handset 50 so long as the cellphone handset is turned on. Event and status messages from the monitor will continue to be sent over the Bluetooth link and received by the cellphone. However, the messages will not be sent to the monitoring center, but will be stored in memory on the cellphone until cellphone service is restored. When service is restored, the messages stored on the cellphone will be immediately sent to the monitoring center at that time. It is for this reason that the flash card memory of the cellphone is of the same or greater capacity as the memory in the monitor, 2 GB in the above example. This means that if cellphone service is disrupted at nighttime when the day's archive data is being downloaded from the monitor, Bluetooth transmission of the archive to the cellphone can continue even if cellphone service is down. The archive will continue to be transferred from the monitor to the cellphone handset even if cellphone service is down, since the flash card memory 304 of the cellphone has the capacity to store the entire archive and, in a constructed embodiment, up to several days of complete archived data. When cellphone service is restored, the cellphone will automatically resume sending the archive data to the monitoring center.

In analyzing ECG and event data, it is important to record the times of events and waveforms so that all of this patient information can be correlated to make an accurate assessment of the patient's condition. This means that the information must be time-stamped with the time of occurrence of the information and that the information be related to a common time base. The patient data could be time-stamped at the time of its receipt at the monitoring center and related to a common time base there, however, as just mentioned, the wireless communication links can be interrupted, thereby delaying the receipt of data at the monitoring center and resulting in erroneous time stamps. Each monitor has its own time base and on-board clock, and this clock could be used to time-stamp data before it is stored in the monitor's memory or sent to the monitoring center. The monitoring center would thereby have a common time base for data received from a monitor. However, the kit of the preferred embodiment uses two monitors which are exchanged each day, each monitor with its own clock. Accordingly, the clocks of the two monitors could be synchronized prior to delivery of the kit to the patient. But clocks can drift over time, and the two clocks of the two monitors could drift at different rates over time, causing a time base disparity between the two clocks. In the preferred embodiment these problems are addressed, not by adjusting the monitor clocks, but by relating the patient data to the time base of the cellphone network. The cellphone handset periodically sends its cellular network-based time to the monitor(s). When the cellphone time is received by a monitor, the monitor stores the cellphone time and the current monitor time as part of the patient data. When the monitoring center receives the data with this timestamp information, it can correlate the patient data to the cellphone network-based time. The monitoring center, having access to the cellphone network and its time base, can relate the patient data and its cellphone network-based time stamps to its own time base if desired. In this way the data produced by multiple monitors used by a patient is related to a common and reliable time base.

Figure 35:
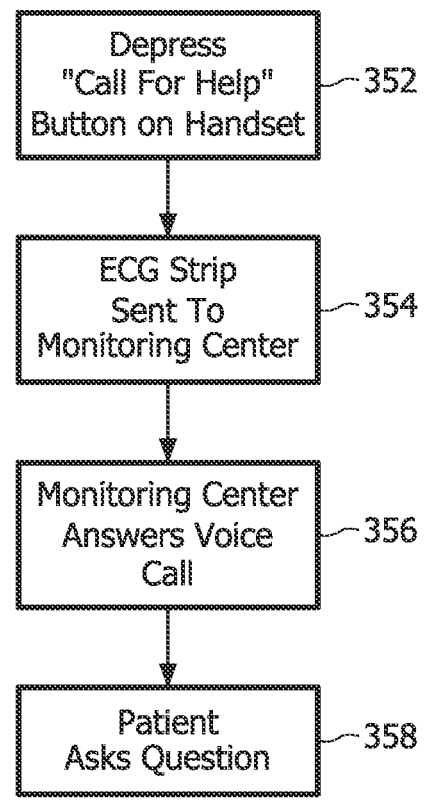
FIG. 35 is a flow diagram of a method for using the "Call for Help" button of a cellphone handset of an ECG monitoring system of the present invention.

As mentioned above, in a constructed embodiment of the present invention there are only two buttons for the patient to operate on the cellphone handset, 62 and 64 as shown in FIG. 6. As previously mentioned, the default functions of these buttons are "Call for Help" and "Record Voice," as indicated by the softkey legends on the screen 58 above the buttons. FIG. 35 provides an example of how the "Call for Help" button can be used in an embodiment of the present invention. The patient will generally be instructed to use the Call for Help button whenever the patient has a problem or question about the monitoring system or has a medical emergency. In either of those situations the patient will depress the Call for Help button 64 on the handset 50, and the cellphone handset will call the monitoring center at 352, the only number it can call in this embodiment. As the call is placed, the monitor 30 is prompted at 354 to begin transmission of an ECG strip to the monitoring center for a 90-second period commencing before the time of the call and continuing for a period of time thereafter. A medical technician at the monitoring center will answer the voice call at 356 and begin talking to the patient. While the technician is talking to the patient he can view the concurrent ECG strip so that the ECG data can be viewed if the patient is calling with a medical problem. In a constructed embodiment of the present invention the technician and the patient can engage in a voice communication at the same time as the ECG strip data is being sent to the monitoring center; it is not necessary to end the voice call so that the ECG data can be sent. If the patient has a question about the monitoring system the question will be asked of the technician as indicated at 358. The technician will provide the requested information or guidance so that the patient can continue to effectively use the monitoring system. If the call is being made in a medical emergency, the technician may call the 911 emergency response system for aid or if appropriate under the conditions, call the patient's physician about the situation. This call-for-help service from the monitoring center should be available to the patient 24 hours a day and seven days a week.

Figure 36:
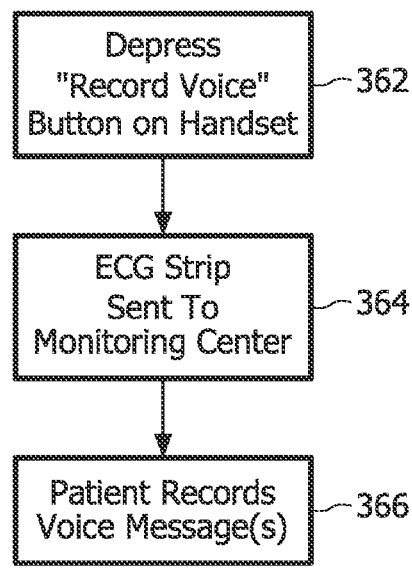
FIG. 36 is a flow diagram of a method for using the "Record Voice" button of a cellphone handset of an ECG monitoring system of the present invention.

FIG. 36 gives an example of the use of the "Record Voice" button 62 of the handset 50. When the patient feels a cardiac symptom as directed by his physician, the patient will use the monitoring system as an event recorder by depressing the Record Voice button at 362. When the button is depressed the patient will listen to instructions from the handset and be told to record a message when the cellphone handset is programmed with these functions. In other embodiments the recording instructions may be provided in a printed user guide supplied with the monitoring kit. If the message has a predetermined maximum length, the patient will be told not to exceed this length or to record a second message if greater recording time is needed. This information may be provided visually or audibly. As the patient speaks into the cellphone microphone the patient's voice is recorded by the cellphone at 366. The depression of the Record Voice button will also cause a command to be issued to the monitor 30 to send a 90-second ECG strip encompassing the time of the voice message at 364. The recorded voice message and the concurrent ECG strip are sent to the monitoring center by the cellphone handset, where an ECG technician can listen to the recorded message from the patient and simultaneously analyze the data of the ECG strip with the ECG viewer.

Figure 37:
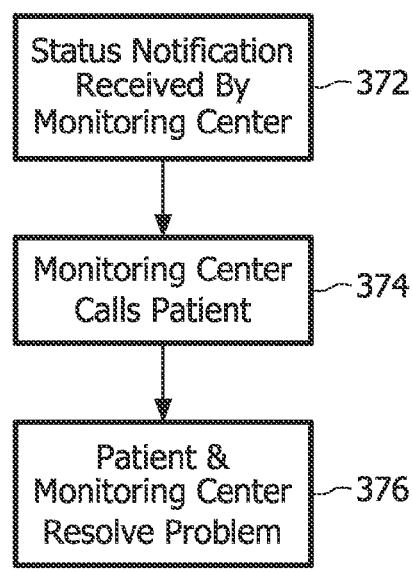
FIG. 37 is a flow diagram of a method for voice contact with a patient to resolve a difficulty reported by an ECG monitoring system of the present invention.

FIG. 37 provides an example of how the monitoring center may respond to a problem reported by the monitoring system. At 372 the monitoring center receives a status notification from the patient's monitor. As mentioned above, in a preferred embodiment the monitor sends a status message to the monitoring center whenever the status of the monitor changes. The status notification may be that an electrode has come loose from the patient's skin or that the monitor has been placed in the charging dock, for example. In the case of these two examples, the cellphone handset alerts the patient that an error condition needs attention and the patient can resolve the problem without intervention by the monitoring center. When a loose electrode is detected by the monitor 30, a message is sent to the cellphone handset 50 and a graphic appears on the cellphone display 58 as illustrated by FIG. 8h, informing the patient of the problem and illustrating how to resolve the problem. The display is accompanied by a tone or beep from the handset, drawing the patient's attention to the displayed message, and may also be accompanied by a voice prompt instructing the patient to take the necessary action. If the patient is unsure what to do, the patient may press an information button "i" on the handset in embodiments having this button, and a context-based voice message is played with a description of the problem shown in the graphic and its resolution. However it is possible that the patient may not notice these messages and the situation continues unresolved; the patient may be asleep, for instance. In such instances the monitoring center may wait a period of time after receipt of the status notification for the patient to resolve the problem. If a period of time has passed without resolution, the ECG viewer may escalate the notification to a higher priority, at which point the monitoring center takes action. The technician at the monitoring center places a call to the patient over the cellphone handset at 374. When the patient answers the cellphone, the technician and the patient discuss the problem and the technician can guide the patient in the resolution of the issue at 376. In this example the resolution may entail replacement of the patch 20 with a new patch, for instance.

In the second example, the patient may have placed the monitor 30 in the charging dock 90 for recharging but forgotten to close the lid 102, which is necessary for recharging to commence in this example. By impedance measurement of the contact engagement the charging dock or monitor will detect that the lid has not been closed to press the monitor into firm engagement with the elastomeric contacts of the charging dock. In other embodiments a switch in the charging dock can detect that the lid has not been closed and a message sent to the monitor of the condition for relay on to the monitoring center. A status notification sent from the monitor is received by the monitoring center at 372, notifying the monitoring center that the monitor has been removed from the patch and/or placed in the charging dock but that recharging has not commenced. The patient is informed locally of this problem, either by the absence of the green charging light in the charging dock or by display or flashing of the LED light 104 of the charging dock in a warning color such as alternate orange and green flashing. A graphic and tone or voice prompt can also be displayed and issued from the cellphone handset 50, alerting the patient to the problem. But if the patient does not tend to the problem after a period of time, the notification received by the monitoring center is escalated to a higher priority on the ECG viewer, at which point the monitoring center can take action. A technician at the monitoring center calls the patient on the cellphone handset 50 and discusses the situation with the patient at 374. The patient and the monitoring center will then resolve the situation by the voice call at 376 when the patient closes the lid 102 of the charging dock and charging of the monitor begins.

For other notifications received by the monitoring center, no patient involvement is needed or appropriate. For instance, if at the end of recharging and archive transmission the self-tests performed by the monitor reveal an error condition in the monitor, the LED light 104 on the charging dock 90 will begin to flash alternately green and orange, informing the patient to contact the monitoring center by using the "Call for Help" button 64 on the cellphone handset. The result of the self-test will also cause the monitor 30 to send a notification of the self-test result to the monitoring center, and if the error condition does not prevent the transmission of the notification, the monitoring center is informed of the problem when the notification is received. A technician at the monitoring center will see the notification and, if the reported condition requires attention, the technician can subsequently call the patient's cellphone handset 50 and instruct the patient to take appropriate action. A replacement monitor may be dispatched to the patient by express courier to replace the monitor with the error condition, for instance. In this case the patient will be instructed to begin using the replacement monitor and to send the monitor with the error condition back to the monitoring center. In other embodiments the patient is provided with both a new monitor and a new cellphone handset which have been Bluetooth-paired. Another alternative is to download the Bluetooth pairing data to the monitor and handset from the monitoring center.

Figure 38:
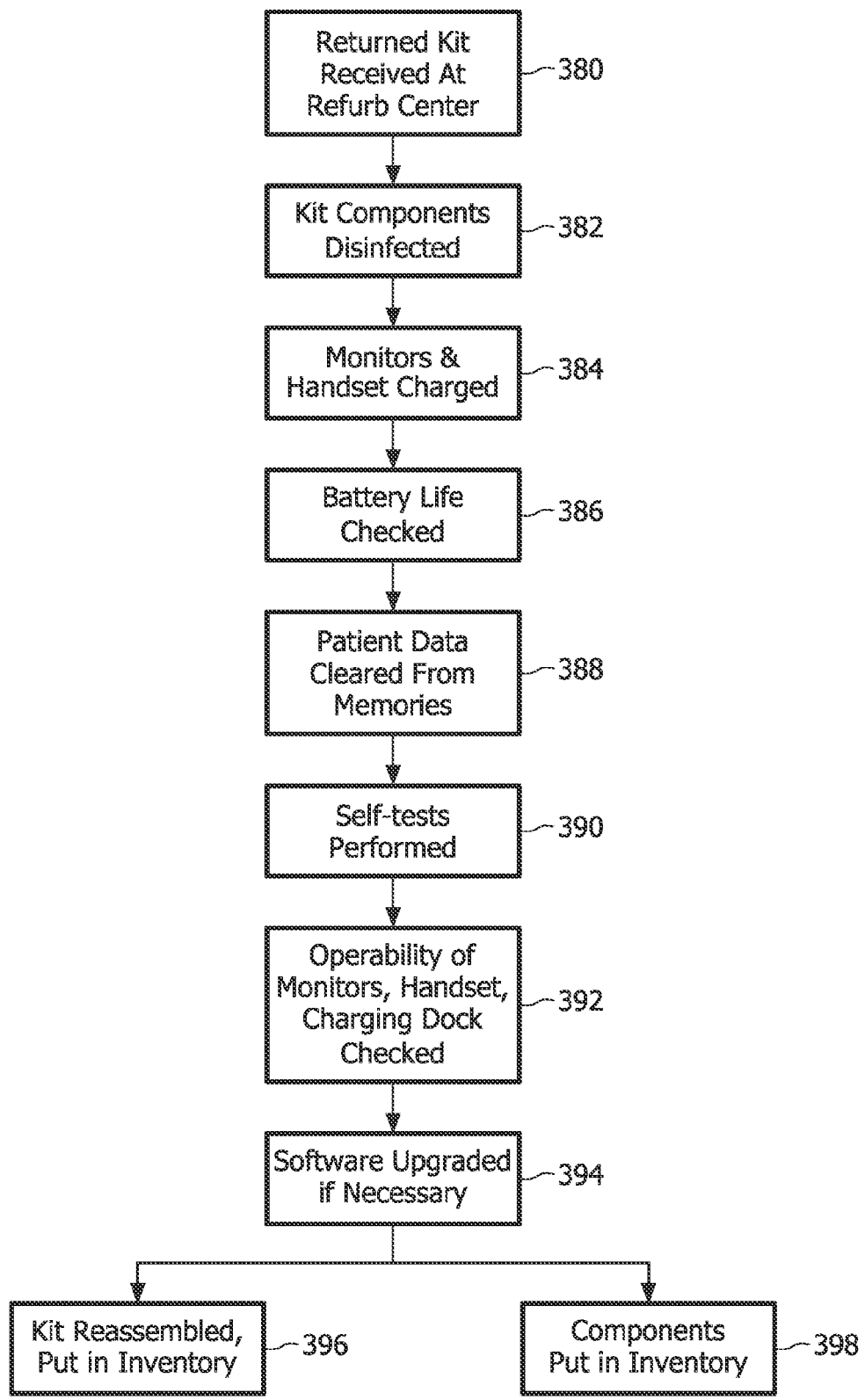
FIG. 38 is a flow diagram of activities performed by a refurbishment center in preparing an ECG monitoring system of the present invention for use by another patient.

A procedure or study conducted with a monitoring system of the present invention will generally continue for twenty-one to thirty days, on average. At the end of the study the patient will return the kit components for reuse by other patients. The patient can take the kit back to the patient's physician at the next office visit, but preferably the kit is supplied with a pre-addressed, postage-paid shipping container or envelope for return of the kit as soon as the study is concluded. The kit can be returned to the monitoring center where it is prepared for the next patient, but preferably the kit is returned to a refurbishment center which specializes in inspecting and preparing kits for subsequent patients. FIG. 38 illustrates some of the procedures performed by such a refurbishment center in preparing a kit for reuse. At 380 the kit is received at a refurbishment center from a postal carrier or transport service. The kit components are unpacked, disinfected at 382 to safeguard against possible exposure to infectious disease, and inventoried to determine that all of the kit components have been returned. A database with screens such as those shown in FIGS. 18, 20 and 22 may be used to log the receipt of the returned kit and its monitors and cellphone handset. If a component is missing the patient or physician is contacted so that the missing component can be returned to the refurbishment center. At 384 the monitor and cell phone batteries are charged, and the batteries of the monitors and cellphone handset are checked at 386 to ensure that they can continue to be recharged to necessary levels during the next study. At 388 any patient data still resident in the memories 216 and 304 of the monitors and cellphone handset is cleared for protection of patient privacy. At 390 the components are self-tested and the self-test results verified. At 392 the kit components are inspected and tested to verify their operability according to specifications. At 394 the software of the charging dock 90, the cellphone handset 50 and the monitors 30 is upgraded if upgrades have become available. As previously mentioned in conjunction with FIG. 12b, in a preferred embodiment the monitors 30 have a USB port accessible through the contacts on the back of the monitor case. New software can be loaded into the monitor by this USB connection. It may also be desirable to re-image the data storage of these devices each time to ensure a fresh software start for each patient. The kit components can be reassembled into a kit at 396 and the kit put back into inventory for subsequent delivery to a new patient. In a preferred embodiment a kit includes two monitors 30, a cellphone handset 50 with cover 56, a charging dock 90 with cellphone charging cord 92 and a power cord, a carrying case for the cellphone handset, a number of patches 20, and a user guide with instructions for the patient. Preferably the kit is delivered to the patient in a box or case which is suitable for shipping the kit back to the refurbishment center, monitoring center, or physician in the same box or case in which the kit was supplied to the patient. Alternatively as indicated at 398, the individual kit components can be put back into inventory for subsequent assembly into a kit as described in conjunction with FIG. 17.

Other variations and features for the present invention will readily occur to those skilled in the art. For instance, cellphones are commercially available with built-in GPS receivers which identify the geographical location of the cellphones. The use of such a cellphone in an implementation of the present invention would enable the location of the cellphone handset to be communicated to the monitoring center, enabling the monitoring center to direct medical assistance to the exact location of the patient if a life-threatening arrhythmia or other medical emergency occurred. Alternatively, cellular triangulation techniques could be used to ascertain the patient's location. For example, if the monitoring center receives an Event notification and ECG strip indicating the occurrence of a serious cardiac event, the technician at the monitoring center will immediately call the patient's cellphone handset to see if the patient needs medical aid. However, the cardiac event may have rendered the patient unconscious and incapable of answering the call from the monitoring center. The control software of the cellphone handset is programmed to answer a call from the monitoring center after a predetermined number of rings, so the connection between the monitoring center and the patient's cellphone will be established even if the patient does not answer the cellphone. In the United States the technician at the monitoring center can then call the local 911 emergency response service, which is able to pinpoint the patient's location from the connection between the monitoring center and the patient's cellphone handset. Medical assistance can be immediately dispatched to the identified location of the stricken patient.

What is claimed is:

1. An electrocardiogram (ECG) monitoring system for cardiac monitoring of an ambulatory patient comprising:
   a battery powered ECG monitor adapted to receive cardiac signals from an electrode attached to a patient, the ECG monitor further including an ECG signal processor operable to detect an arrhythmia from the cardiac signals, a memory for storing an archive of processed ECG signals, and a transceiver for wirelessly transmitting ECG signal data corresponding to the arrhythmia;
   a cellphone handset including cellphone electronics operable for communication over a cellular network and a transceiver for wirelessly receiving ECG signal data and archive data from the ECG monitor; and
   a charging dock to which the ECG monitor is coupled when not receiving cardiac signals from a patient, the charging dock being operable to recharge the battery of the battery powered ECG monitor,
   wherein the ECG monitor is further operable to sense a coupling to the charging dock and to sense an engagement to the electrode, and further wherein the ECG monitor is operable to wirelessly transmit the archive of ECG signals stored in the memory to the cellphone handset responsive to the sensed coupling and to wirelessly transmit the ECG signal data to the cellphone handset responsive to the sensed engagement.

2. The ECG monitoring system of claim 1, wherein the cellphone handset is further responsive to the receipt of the archive of ECG signals from the ECG monitor for sending the archive of ECG signals to a monitoring center over the cellular network.

3. The ECG monitoring system of claim 1, wherein the ECG monitor is further operable, following transmission of the archive of ECG signals stored in the memory to the cellphone handset, to clear the stored archive of ECG signals from the memory.

4. The ECG monitoring system of claim 1, wherein the charging dock is further operable to recharge the cellphone handset while a battery of the battery powered ECG monitor is being recharged.

5. The ECG monitoring system of claim 1, wherein the ECG monitor further includes a processor for automatically performing a self-test of the ECG monitor when the ECG monitor has been coupled to the charging dock for recharging.

6. The ECG monitoring system of claim 5, wherein the self-test is performed at a conclusion of recharging by the charging dock.

7. The ECG monitoring system of claim 1, wherein the charging dock is operable to recharge a battery of the battery powered ECG monitor after verification that the ECG monitor has been properly coupled to the charging dock.

8. The ECG monitoring system of claim 1, wherein the ECG monitor further includes a plurality of electrical contacts coupled to the battery; and
   wherein the charging dock further includes a compartment into which the ECG monitor is located for recharging;
   a plurality of contacts located in the compartment which engages ECG monitor contacts for recharging when the ECG monitor is properly located in the compartment; and
   a lid which must be closed during recharge of a battery of the ECG monitor.

9. The ECG monitoring system of claim 8, wherein the ECG monitor is keyed for proper placement in the compartment; and
   wherein the compartment is correspondingly keyed to engage the keying of the ECG monitor when the ECG monitor is properly placed in the compartment.

10. The ECG monitoring system of claim 8, further comprising circuitry adapted to verify that electrical contacts of the ECG monitor are properly engaged with the contacts located in the compartment of the charging dock.

11. The ECG monitoring system of claim 10, wherein electrical contacts of the ECG monitor are properly engaged with the contacts located in the compartment only when the lid is closed.

12. The ECG monitoring system of claim 1, wherein the charging dock further comprises a light which is illuminated while the battery of the ECG monitor is being recharged.

13. The ECG monitoring system of claim 12, wherein illumination of the light is changed when recharge of the battery of the ECG monitor is unsuccessful.

14. The ECG monitoring system of claim 13, wherein the ECG monitor is further operable to perform a self-test at a conclusion of recharging;
   wherein a illumination of the light is changed when a result of the self-test is undesirable.

15. The ECG monitoring system of claim 12,
   wherein a illumination of the light is changed when the transmitted archive of ECG signals is not properly received.

16. The ECG monitoring system of claim 1, wherein ECG monitor further comprises a plurality of electrical contacts coupled to the ECG signal processor; and
   wherein the charging dock is further operable to apply test signals to the electrical contacts for testing of the ECG signal processor of the ECG monitor.

17. The ECG monitoring system of claim 1, further comprising a second battery powered ECG monitor which is also be recharged by the charging dock,
   wherein the second battery powered ECG monitor receives cardiac signals from the patient while the first ECG monitor is being recharged by the charging dock.

\* \* \* \* \*